United States Patent
Brodnick

(10) Patent No.: US 9,078,572 B2
(45) Date of Patent: Jul. 14, 2015

(54) HEARTBEAT DETECTION AND CATEGORIZATION

(71) Applicant: APN Health, LLC, Pewaukee, WI (US)

(72) Inventor: Donald Brodnick, Cedarburg, WI (US)

(73) Assignee: APN Health, LLC, Pewaukee, WI (US)

( * ) Notice: Subject to any disclaimer, the term of this patent is extended or adjusted under 35 U.S.C. 154(b) by 22 days.

(21) Appl. No.: 14/067,561

(22) Filed: Oct. 30, 2013

(65) Prior Publication Data

US 2015/0119736 A1    Apr. 30, 2015

(51) Int. Cl.
 *A61B 5/04* (2006.01)
 *A61B 5/044* (2006.01)
 *A61B 5/0456* (2006.01)

(52) U.S. Cl.
 CPC ............ *A61B 5/04011* (2013.01); *A61B 5/044* (2013.01); *A61B 5/04017* (2013.01); *A61B 5/0456* (2013.01)

(58) Field of Classification Search
 CPC ............ A61B 5/04011; A61B 5/0456; A61B 5/04525
 See application file for complete search history.

(56) References Cited

U.S. PATENT DOCUMENTS

| | | | |
|---|---|---|---|
| 3,939,824 A * | 2/1976 | Arneson et al. ............... | 600/485 |
| 4,240,442 A | 12/1980 | Andresen et al. | |
| 4,374,382 A | 2/1983 | Markowitz | |
| 4,583,553 A | 4/1986 | Shah et al. | |
| 5,117,824 A | 6/1992 | Keimel et al. | |
| 5,365,426 A | 11/1994 | Siegel et al. | |
| 5,462,060 A | 10/1995 | Jacobson et al. | |
| 5,526,813 A | 6/1996 | Yoshida | |
| 5,560,367 A | 10/1996 | Haardt et al. | |
| 5,560,368 A | 10/1996 | Berger | |

(Continued)

FOREIGN PATENT DOCUMENTS

| | | |
|---|---|---|
| EP | 1745740 A1 | 1/2007 |
| EP | 2047794 A1 | 4/2009 |

(Continued)

OTHER PUBLICATIONS

Pan et al. A Real-Time QRS Detection Algorithm. IEEEE Transactions on Biochemical Engineering. vol. BME-32, No. 3, Mar. 1985. <http://mirel.xmu.edu.cn/mirel/public/Teaching/QRSdetection.pdf>.

(Continued)

*Primary Examiner* — George Evanisko

(74) *Attorney, Agent, or Firm* — Jansson Munger McKinley and Shape Ltd.

(57) ABSTRACT

An automatic method for detecting heartbeats of a patient from two or more selected ECG signals, the method comprising: (a) determining a velocity for each of the selected signals; (b) summing together absolute values of each of the velocities; (c) comparing the sum with a threshold T having a value about one-half of an expected maximum value of the sum; and (d) if the sum is greater than the threshold T and if elapsed time since an immediately-previous heartbeat detection is greater than a preset refractory period $t_R$, a heartbeat has been detected at a time $t_D$ of the velocity determinations. The method also further includes steps by which the detected heartbeats are categorized based on the velocities at the time of detection.

45 Claims, 20 Drawing Sheets

(56) References Cited

U.S. PATENT DOCUMENTS

| | | |
|---|---|---|
| 5,701,907 A | 12/1997 | Klammer |
| 6,236,883 B1 | 5/2001 | Ciaccio et al. |
| 6,526,313 B2 | 2/2003 | Sweeney et al. |
| 6,556,860 B1 | 4/2003 | Groenewegen |
| 6,937,888 B2 | 8/2005 | Kohler et al. |
| 7,364,550 B1 | 4/2008 | Turcott |
| 7,561,912 B2 | 7/2009 | Schatz et al. |
| 7,610,084 B2 | 10/2009 | Sweeney et al. |
| 7,792,571 B2 | 9/2010 | Sweeney et al. |
| 7,890,170 B2 | 2/2011 | Ettori et al. |
| 8,041,417 B2 | 10/2011 | Jonckheere et al. |
| 8,064,995 B1 | 11/2011 | Dupelle et al. |
| 8,137,269 B2 | 3/2012 | Sheikhzadeh-Nadjar et al. |
| 8,150,503 B2 | 4/2012 | Schatz et al. |
| 2002/0133085 A1 | 9/2002 | Kohler et al. |
| 2002/0138013 A1 | 9/2002 | Guerrero et al. |
| 2003/0216654 A1 | 11/2003 | Xu et al. |
| 2004/0015090 A1 | 1/2004 | Sweeney et al. |
| 2004/0059203 A1 | 3/2004 | Guerrero et al. |
| 2004/0186388 A1 | 9/2004 | Gerasimov |
| 2005/0245973 A1 | 11/2005 | Sherman |
| 2007/0161916 A1 | 7/2007 | Zantos et al. |
| 2008/0109041 A1 | 5/2008 | de Voir |
| 2009/0099468 A1 | 4/2009 | Thiagalingam et al. |
| 2010/0041975 A1 | 2/2010 | Chen et al. |
| 2010/0305645 A1 | 12/2010 | Sweeney et al. |
| 2011/0071375 A1 | 3/2011 | Baker, Jr. et al. |
| 2011/0137153 A1 | 6/2011 | Govari et al. |
| 2011/0172729 A1 | 7/2011 | Sweeney et al. |
| 2011/0282226 A1 | 11/2011 | Benser et al. |
| 2011/0288605 A1 | 11/2011 | Kaib et al. |
| 2012/0035488 A1 | 2/2012 | MacAdam et al. |
| 2012/0101398 A1 | 4/2012 | Ramanathan et al. |
| 2012/0123279 A1 | 5/2012 | Brueser et al. |
| 2012/0130263 A1 | 5/2012 | Pretorius et al. |
| 2012/0179055 A1 | 7/2012 | Tamil et al. |
| 2012/0184864 A1 | 7/2012 | Harlev et al. |
| 2012/0197151 A1 | 8/2012 | Schatz et al. |
| 2013/0006131 A1 | 1/2013 | Narayan et al. |
| 2013/0030314 A1 | 1/2013 | Keel et al. |
| 2013/0066221 A1 | 3/2013 | Ryu et al. |
| 2013/0109945 A1 | 5/2013 | Harlev et al. |
| 2013/0245477 A1 | 9/2013 | Brodnick et al. |

FOREIGN PATENT DOCUMENTS

| | | |
|---|---|---|
| WO | 9619939 A1 | 7/1996 |
| WO | 2005002669 A2 | 1/2005 |
| WO | 2011088043 A1 | 7/2011 |
| WO | 2012056342 A2 | 5/2012 |

OTHER PUBLICATIONS

Friesen G.M. et al. "A Comparison of the Noise Sensitivity of None QRS Detection Alogrithyms," IEEE Transactions on Biomedical Engineering, IEEE Inc. New York, US, Bd. 37, Nr. 1, 1990, Seiten 85-98.

\* cited by examiner

LEGEND $x_c(t)$ = analog ECG channel signals (N channels)
$i$ = time index of digital signal streams
$x_c(t_i)$ = digital ECG channel signals
$f_c(t_i)$ = intermediate digital ECG channel signals
$|x|$ = ABS(x) = absolute value of x
$g_c(t_i)$ = filtered ECG channel signals = $|f_c(t_i)|$
$G(t_i)$ = sum of all $g_c(t_i)$ = velocity sum
$k$ = number of time samples in a boxcar sum
$T$ = threshold (initial value in example = 1000)
$G_{max}$ = maximum value of summed signal $G(t_i)$
 during the most recent $t_m$-second period
 ($t_m$-second time periods are consecutive,
 not moving-window periods)
$t_m$ = preset time period of $timer_m$*
$t_R$ = refractory period ($timer_R$**)
$t_L$ = detection failure time limit ($timer_L$)
$F(t_D)$ = vector having components $f_c(t_D)$,
 at time of heartbeat detection $t_i = t_D$
$SVM_D$ = squared vector magnitude (dot product
 of $F(t_D)$ with itself: [$F(t_D) \cdot F(t_D)$]
$Q$ = number of possible templates
$q$ = index of heartbeat-category template vectors
$F_q$ = heartbeat-category template vector q
$SVM_q$ = squared vector magnitude (dot product
 of $F_q$ with itself: [$F_q \cdot F_q$]
$DP_q$ = dot product of F(tD) with template
 vector q: [$F(t_D) \cdot F_q$]
$SCDA_q$ = signed squared cosine difference angle
$SC_M$ = maximum value of $SCDA_q$
$SC_L$ = limit value of $SCDA_q$ defining template
 categories (threshold angle = $\theta_L$)
$q_E$ = index of empty template vector slot
$q_M$ = index of template vector with $SC_M$
$C_q$ = count of heartbeats matching template
 vector $F_q$
$F_E = F_q$ at $q = q_E$; $F_M = F_q$ at $q = q_M$
$SVM_E = SVM_q$ at $q = q_E$; $SVM_M = SVM_q$ at $q = q_M$
$C_E = C_q$ at $q = q_E$; $C_M = C_q$ at $q = q_M$ \* $timer_m$ is a countdown timer
\*\* refractory $timer_R$ is an elapsed-time timer sampling rate $f_s$ = 1,000sps ($\Delta t$ = 1msec); N = 3;
k = 20; $t_m$ = 2sec; $t_R$ = 120msec: $t_L$ = 5sec

FIG. 4

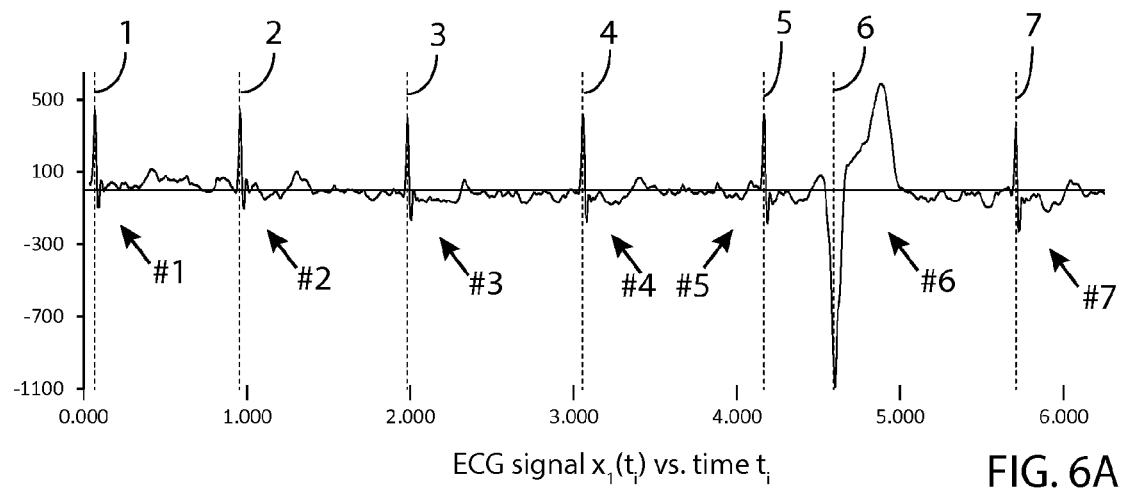
ECG signal $x_1(t_i)$ vs. time $t_i$                FIG. 6A
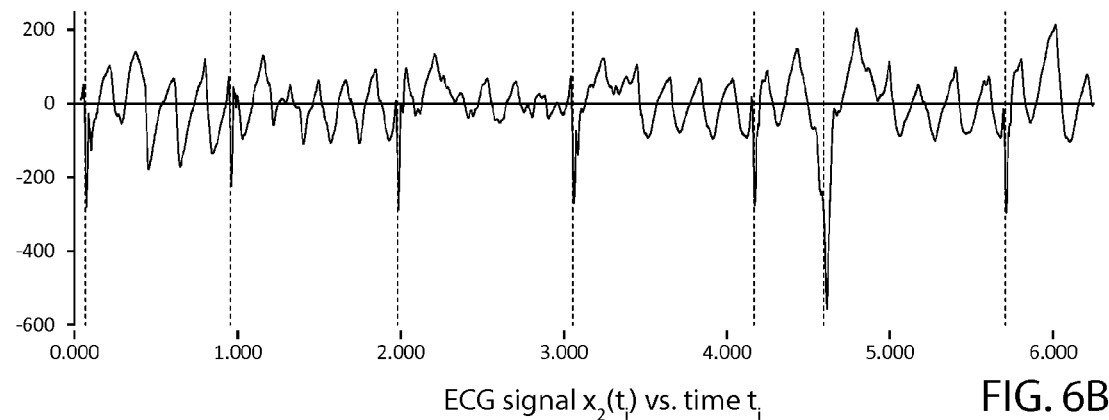
ECG signal $x_2(t_i)$ vs. time $t_i$                FIG. 6B
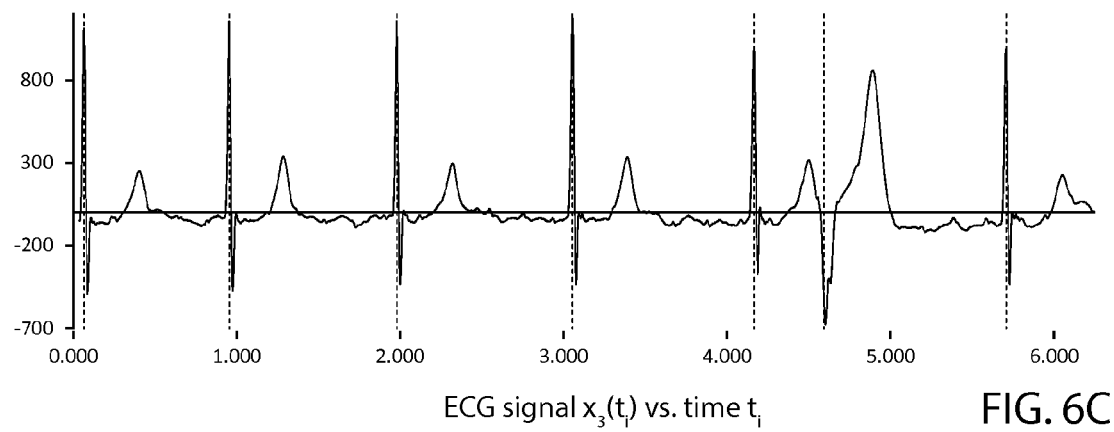
ECG signal $x_3(t_i)$ vs. time $t_i$                FIG. 6C

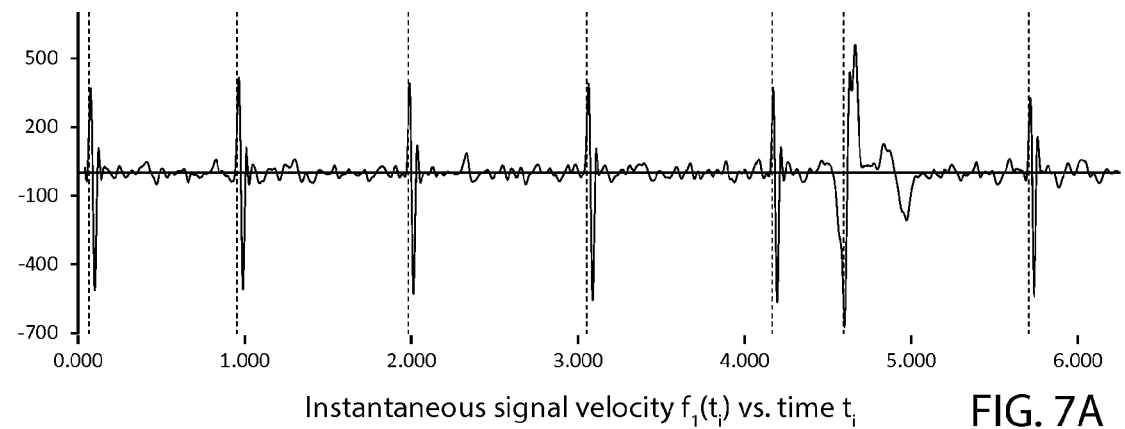
Instantaneous signal velocity $f_1(t_i)$ vs. time $t_i$     FIG. 7A
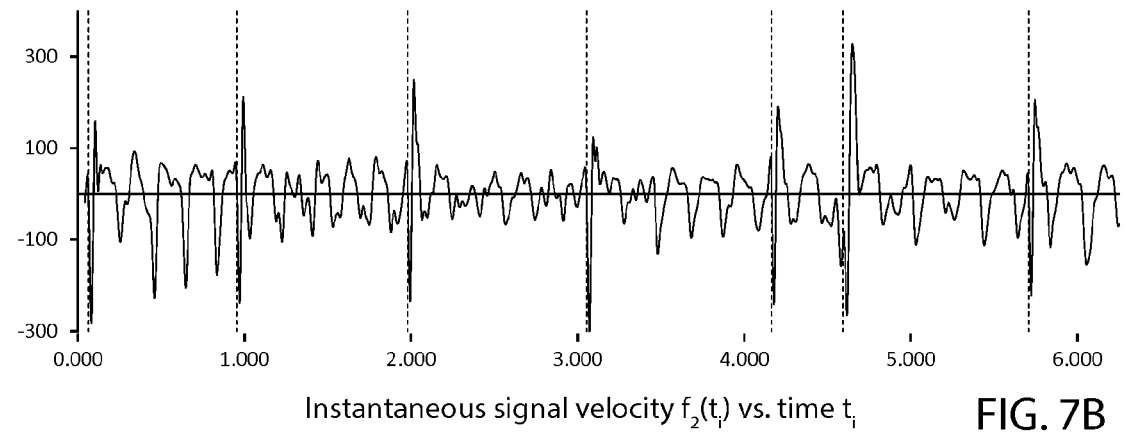
Instantaneous signal velocity $f_2(t_i)$ vs. time $t_i$     FIG. 7B
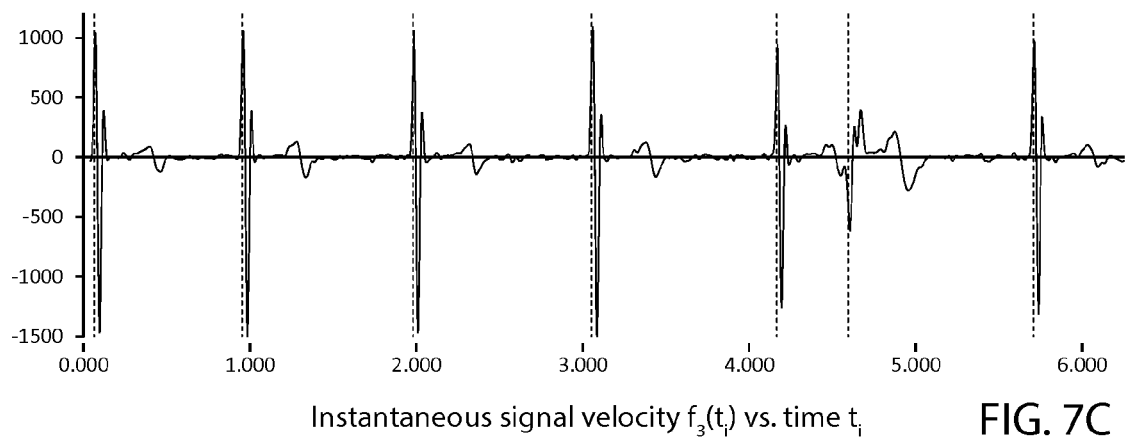
Instantaneous signal velocity $f_3(t_i)$ vs. time $t_i$     FIG. 7C Absolute velocity $g_1(t_i)$ vs. time $t_i$ Absolute velocity $g_2(t_i)$ vs. time $t_i$ Absolute velocity $g_3(t_i)$ vs. time $t_i$

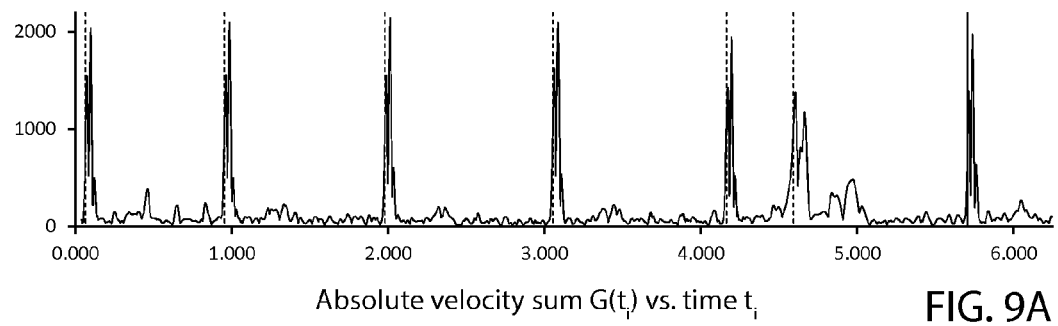
Absolute velocity sum G(t$_i$) vs. time t$_i$          FIG. 9A
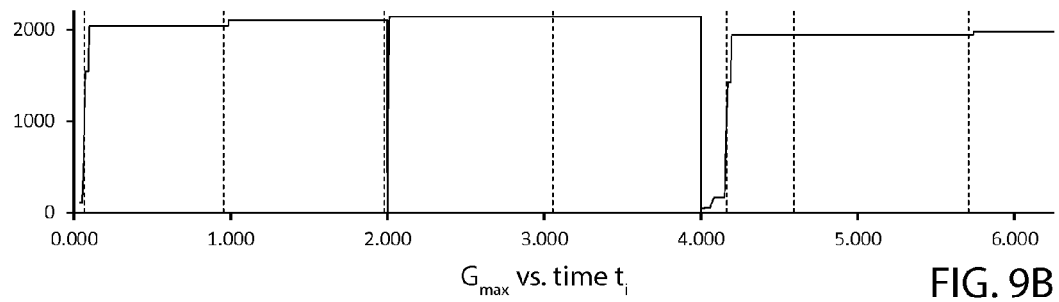
G$_{max}$ vs. time t$_i$          FIG. 9B
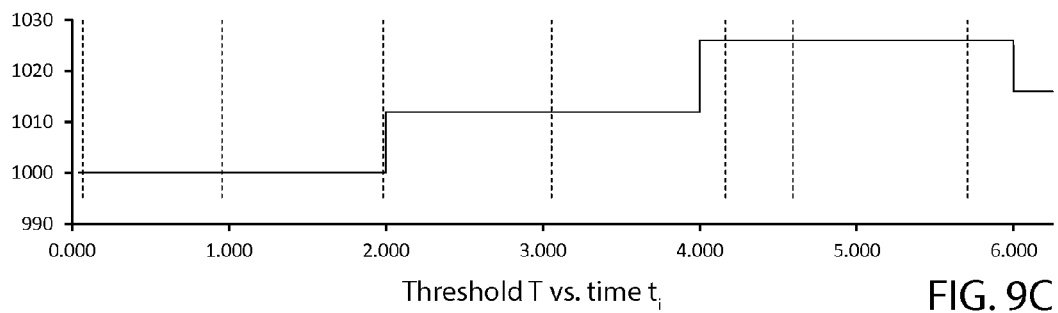
Threshold T vs. time t$_i$          FIG. 9C
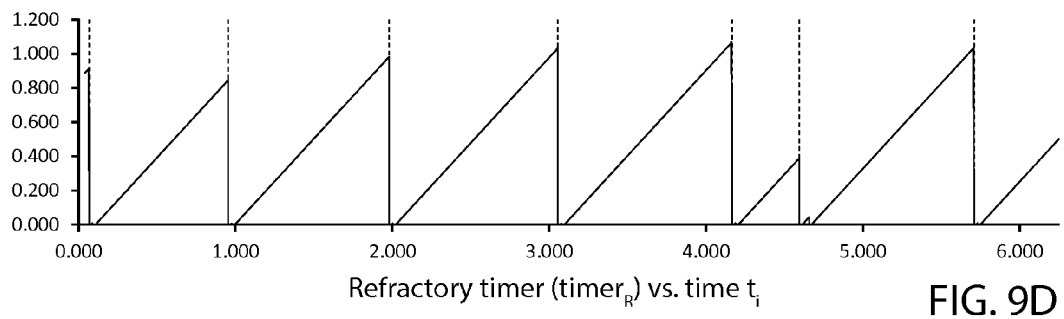
Refractory timer (timer$_R$) vs. time t$_i$          FIG. 9D

FIG. 10A

| | $t_D$ | $f_1(t_D)$ | $f_2(t_D)$ | $f_3(t_D)$ | $SVM_D$ |
|---|---|---|---|---|---|
| Heartbeat #1 | 0.066 | 186 | -13 | 813 | 695734 |
| Heartbeat #2 | 0.954 | 201 | 38 | 813 | 702814 |
| Heartbeat #3 | 1.980 | 204 | 30 | 820 | 714916 |
| Heartbeat #4 | 3.054 | 208 | 11 | 822 | 719069 |
| Heartbeat #5 | 4.165 | 239 | 26 | 789 | 680318 |
| Heartbeat #6 | 4.593 | -559 | -100 | -384 | 469937 |
| Heartbeat #7 | 5.708 | 223 | 2 | 852 | 775637 |
| | | | | | |
| Template 8 | | -551 | -246 | -124 | 379493 |
| Template 7 | | 186 | -13 | 813 | 695734 |
| Template 6 | | -559 | -100 | -384 | 469937 |

FIG. 10B

| | $DP_8$ | $SCDA_8$ | $\theta_8$ (°) | $DP_7$ | $SCDA_7$ | $\theta_7$ (°) | $DP_6$ | $SCDA_6$ | $\theta_6$ (°) | category |
|---|---|---|---|---|---|---|---|---|---|---|
| Heartbeat #1 | -200100 | -0.1517 | 112.92 | | | | | | | new 7 |
| Heartbeat #2 | -220911 | -0.1830 | 115.33 | 697861 | 0.9960 | 3.63 | | | | 7 |
| Heartbeat #3 | -221464 | -0.1808 | 115.16 | 704214 | 0.9970 | 3.12 | | | | 7 |
| Heartbeat #4 | -219242 | -0.1761 | 114.82 | 706831 | 0.9987 | 2.10 | | | | 7 |
| Heartbeat #5 | -235921 | -0.2156 | 117.67 | 685573 | 0.9930 | 4.80 | | | | 7 |
| Heartbeat #6 | 380225 | 0.8107 | 25.79 | -414866 | -0.5264 | 136.51 | -452025 | -0.5606 | 138.48 | new 6 |
| Heartbeat #7 | -229013 | -0.1782 | 114.97 | 734128 | 0.9987 | 2.05 | | | | 7 |

ECG signal $x_1(t_i)$ vs. time $t_i$

ECG signal $x_2(t_i)$ vs. time $t_i$

ECG signal $x_3(t_i)$ vs. time $t_i$

Absolute velocity sum $G(t_i)$ vs. time $t_i$

FIG. 17A

| | $t_D$ | $f_1(t_D)$ | $f_2(t_D)$ | $f_3(t_D)$ | $f_1(t_{D+20})$ | $f_2(t_{D+20})$ | $f_3(t_{D+20})$ | $SVM_D$ |
|---|---|---|---|---|---|---|---|---|
| Heartbeat #1 | 0.066 | 186 | -13 | 813 | 73 | -251 | -394 | 919300 |
| Heartbeat #2 | 0.954 | 201 | 38 | 813 | 147 | -216 | -349 | 892880 |
| Heartbeat #3 | 1.980 | 204 | 30 | 820 | 79 | -190 | -365 | 890482 |
| Heartbeat #4 | 3.054 | 208 | 11 | 822 | 79 | -280 | -261 | 871831 |
| Heartbeat #5 | 4.165 | 239 | 26 | 789 | -77 | -188 | -321 | 824632 |
| Heartbeat #6 | 4.593 | -559 | -100 | -384 | -360 | -227 | -457 | 859915 |
| Heartbeat #7 | 5.708 | 223 | 2 | 852 | -132 | -157 | -507 | 1074759 |
| Template 8 | | -551 | -246 | -124 | -125 | -213 | -129 | 457128 |
| Template 7 | | 186 | -13 | 813 | 73 | -251 | -394 | 919300 |
| Template 6 | | 239 | 26 | 789 | -77 | -188 | -321 | 824632 |
| Template 6 | | -559 | -100 | -384 | -360 | -227 | -457 | 859915 |

FIG. 17B

| | $DP_8$ | $SCDA_8$ | $\theta_8(°)$ | $DP_7$ | $SCDA_7$ | $\theta_7(°)$ | $DP_6$ | $SCDA_6$ | $\theta_6(°)$ | $DP_5$ | $SCDA_5$ | $\theta_5(°)$ | category |
|---|---|---|---|---|---|---|---|---|---|---|---|---|---|
| Heartbeat #1 | -104936 | -0.026 | 99.32 | | 0.988 | 6.42 | | | | | | | new 7 |
| Heartbeat #2 | -148257 | -0.054 | 103.42 | 900314 | 0.993 | 4.89 | | | | | | | 7 |
| Heartbeat #3 | -143784 | -0.051 | 103.02 | 901481 | 0.979 | 8.37 | | | | | | | 7 |
| Heartbeat #4 | -135808 | -0.046 | 102.42 | 885712 | 0.961 | 11.36 | | | | | | | 7 |
| Heartbeat #5 | -144843 | -0.056 | 103.65 | 853614 | -0.053 | 103.27 | | | | | | | new 6 |
| Heartbeat #6 | 532529 | 0.721 | 31.86 | -204111 | 0.940 | 14.19 | -222084 | -0.070 | 105.29 | -137167 | -0.020 | 98.20 | new 5 |
| Heartbeat #7 | -113669 | -0.026 | 99.33 | 963657 | | | 928004 | 0.972 | 9.69 | | | | 6 |

HEARTBEAT DETECTION AND CATEGORIZATION

FIELD OF THE INVENTION

This invention is related generally to the field of electrophysiology, and more particularly to technology for accurate measurement of parameters within ECG electrical signals such as heart rates and the nature of individual heartbeats.

BACKGROUND OF THE INVENTION

The invention disclosed herein involves the processing of multiple channels of electrical signals which are produced by the heart. These channel signals primarily include the ECG signals from body-surface electrodes although signals from electrodes within the body, i.e., intracardiac signals from within vessels and chambers of the heart and epicardial signals from the outer surface of the heart may also be among the cardiac signals processed. Throughout this document the term "ECG signal" is used to refer to all of these types of channel signals since the inventive method is primarily intended to be used with body-surface electrodes. Such use of terminology is not intended to be limiting to the scope of the invention.

Numerous methods for signal processing of heartbeats are known. Among these are methods disclosed in the following patent applications: PCT International Patent Application No. PCT/US 12/54265 filed on Sep. 7, 2012 and entitled "R-Wave Detection Method;" U.S. patent application Ser. No. 13/842,994 filed on Mar. 15, 2013 and entitled "Multi-Channel Cardiac Measurements;" U.S. patent application Ser. No. 13/888,070 filed on May 5, 2013 and entitled "Multi-Channel Cardiac Measurements;" and U.S. patent application Ser. No. 13/922,953 filed on Jun. 20, 2013 and entitled "Multi-Channel Cardiac Measurements." Each of these applications are in whole or in part invented by the inventor of the present invention and are commonly owned by APN Health, LLC of Pewaukee, Wis. None of these applications combine signals of multiple cardiac channels in the heartbeat detection process prior to performing a threshold comparison. None of these inventions includes steps which categorize the detected heartbeats into categories having similar heartbeat morphologies or shapes.

Other current technology which involves heartbeat detection and categorization relates to systems for post-processing of ECG signals captured by a Holter monitor. These systems typically involve the processing of ECG signals using values of such signals at more than one point in time within an individual heartbeat. In contrast, the present invention depends on measurements at a single instant in time in order to detect and categorize heartbeats, allowing this inventive system to detect heartbeats very early in the time period of the heartbeat and to operate essentially in real time.

Categorizing heartbeats into groups having similar morphologies in essentially real time enables a cardiologist to very quickly identify the frequency of occurrence of various ectopic heartbeats, particularly for patients undergoing interventional procedures to alleviate the causes of such heartbeats. Among the ectopic heartbeats which are of importance are: premature ventricular contractions (PVC); premature atrial contractions (PAC); various types of bundle branch blocks; ventricular escape beats; junctional escape beats; fusion beats; and paced beats.

PVC and PAC heartbeats (also known by several other names) are among the most common ectopic heartbeats and when they occur as individual beats rather than in a series of repetitive beats, are not considered to be clinically significant. Such individual beats commonly occur in healthy young and elderly patients without heart disease. However, when ectopic beats recur on a much more regular basis, interventional treatment or procedures may be undertaken to alleviate such cardiac abnormalities. The present invention is an important advance in the technology of cardiac diagnosis and treatment by providing a rapid and reliable method for heartbeat detection and categorization.

OBJECTS OF THE INVENTION

It is an object of the inventive automatic method of heartbeat detection to provide a reliable method for detection of heartbeats.

Another object of the inventive method is to provide an automatic method by which heartbeats can be categorized into predefined classes of heartbeats.

Another object of the inventive method is to provide an automatic method by which heartbeats can be categorized into a set of adaptively-defined classes of heartbeats based on a patient's specific heartbeats.

Another object of the inventive method is to provide an automatic method of heartbeat detection that is able to detect heartbeats on the leading edge of a heartbeat.

Another object of the inventive method is to provide an automatic method of heartbeat detection which adapts to signal-level changes in ECG signals.

Another object of the inventive method is to provide an automatic method by which premature ventricular contractions can be identified, characterized, and counted.

Another object of the inventive method of automatic heartbeat detection is to detect heartbeats in near real-time (very short processing delay).

Another object of the inventive automatic heartbeat detection method is to detect heartbeats using features of ECG signals with which cardiologists are familiar.

Still another object of the inventive method is to provide an automatic method of heartbeat detection which displays useful heartbeat detection and characterization information to a cardiologist.

Yet another object of this invention is to provide a method of heartbeat detection which is applicable to post-processing of data recorded by a Holter monitor.

These and other objects of the invention will be apparent from the following descriptions and from the drawings.

SUMMARY OF THE INVENTION

The invention is an automatic method for detecting heartbeats of a patient from two or more selected ECG signals. The method comprises (a) determining a velocity for each of the selected signals, (b) summing together absolute values of each of the velocities, (c) comparing the sum with a threshold T having a value about one-half of an expected maximum value of the sum, and (d) if the sum is greater than the threshold T and if elapsed time since an immediately-previous heartbeat detection is greater than a preset refractory period $t_R$, a heartbeat has been detected at a time $t_D$ of the velocity determinations. With these steps, this invention detects a heartbeat with a velocity measurement during the initial portion of the heartbeat.

In highly-preferred embodiments of the inventive method, when a heartbeat has been detected, the method further includes the steps of (i) forming a vector $F(t_D)$ having as its components the velocities of each of the selected signals at time $t_D$, (ii) determining the angle between the vector $F(t_D)$ and a previously-stored template vector, (iii) comparing the angle with a threshold angle, and (iv) if the angle is less than the threshold angle, categorizing the heartbeat as similar to a heartbeat which corresponds to the template vector.

In certain preferred embodiments of the inventive method, angle determination and comparison include the steps of (1) computing a squared vector magnitude $SVM_D$ as the dot product of $F(t_D)$ with itself, (2) computing the dot product $DP_q$ of $F(t_D)$ with a template vector $F_q$, (3) computing a squared vector magnitude $SVM_q$ as the dot product of $F_q$ with itself, (4) computing a signed squared cosine difference angle $SCDA_q$ as $SCDA_q=sgn(DP_q)*DP_q*DP_q/(SVM_D*SVM_q)$, and (5) comparing $SCDA_q$ with a squared cosine threshold $SC_L$. (As used herein, the * symbol indicates multiplication.) In certain of these embodiments, the inventive method further includes comparing the vector $F(t_D)$ with a plurality of template vectors to determine if the vector $F(t_D)$ is within the threshold angle of any of the plurality of template vectors. In some of these embodiments, if the angle between the vector $F(t_D)$ and more than one of the plurality of template vectors is less than the threshold angle, the heartbeat is categorized as similar to a heartbeat which corresponds to the template vector having the smallest angle between itself and the vector $F(t_D)$. Further, in some embodiments, if the angle between the vector $F(t_D)$ and each of the plurality of template vectors is greater than or equal to the threshold angle, a template vector having $F_q=F(t_D)$ is added to the plurality of template vectors.

In certain preferred embodiments of the inventive method, the vector $F(t_D)$ is compared with a plurality of template vectors to determine if the vector $F(t_D)$ is within the threshold angle of any of the plurality of template vectors.

In certain embodiments, if the angle between the vector $F(t_D)$ and more than one of the plurality of template vectors is less than the threshold angle, the heartbeat is categorized as similar to a heartbeat which corresponds to the template vector having the smallest angle between itself and the vector $F(t_D)$. Further, in some embodiments, if the angle between the vector $F(t_D)$ and each of the plurality of template vectors is greater than or equal to the threshold angle, a template vector $F_q=F(t_D)$ is added to the plurality of template vectors.

In certain embodiments of the automatic heartbeat detection method, each of the template vectors has a threshold angle associated therewith, not all of which have the same angle value.

In some embodiments, at least a portion of the template vectors are preset template vectors and in some of these embodiments, all of the template vectors are preset vectors.

Certain highly-preferred embodiments of the automatic heartbeat detection method further include a slot-plurality of template vector slots, the slot-plurality being greater than or equal to the plurality of template vectors, and each template vector is in a corresponding template vector slot. In such embodiments, if the vector $F(t_D)$ is not within the threshold angle of any of the plurality of template vectors and an empty template vector slot is available, a new template vector $F_q=F(t_D)$ is added to the plurality of template vectors. In some of these embodiments, if no empty template vector slot is available, one of the template vectors is replaced with a new template vector $F_q=F(t_D)$.

Highly-preferred embodiments include storing of categorized heartbeats, and also may include displaying information descriptive of one or more stored heartbeats.

In highly-preferred embodiments of the inventive method for heartbeat detection, determining the velocity of each of the selected signals includes digitizing each of the selected signals and filtering each of the digitized signals to generate the velocity for each selected signal. In certain of these embodiments, the filter is a first-difference filter, which in some embodiments is a boxcar filter.

In highly-preferred embodiments of the inventive method, the threshold T is adjusted based on the maximum velocity sum during a preset time period $t_m$. In some of these embodiments, when the preset time period $t_m$ has elapsed, if a preset detection failure time limit $t_L$ has not elapsed since previous heartbeats were detected, the threshold T is determined by computing $T=T_p+(G_{max}/2-T_p)/4$ where $G_{max}$ is the maximum velocity sum during the elapsed preset time period $t_m$ and $T_p$ is the previous value of the threshold T. Further, in some embodiments, when preset time period $t_m$ has elapsed, if a preset detection failure time limit $t_L$ has elapsed since previous heartbeats were detected, the threshold T is set to $G_{max}/2$.

In some preferred embodiments, $t_R$ is about 120 milliseconds, $t_m$ is about 2 seconds, and $t_L$ is about 5 seconds.

In certain preferred embodiments, three ECG signals are selected, and the signals form a quasi-orthogonal set.

In some preferred embodiments, the patient is in a non-sedated state and the inventive method further includes the step of providing interventional treatment to the patient in a sedated state based on heartbeats categorized while the patient was in the non-sedated state.

In some highly-preferred embodiments of the automatic heartbeat detection method, the ECG signals further include one or more ECG signals in addition to the selected ECG signals, and the method includes storing one or more of the additional ECG signals. In some of these embodiments, the method further includes displaying information descriptive of a detected heartbeat.

In another aspect, the automatic heartbeat detection method further includes, when a heartbeat has been detected, the steps of: (a) forming a vector $F(t_D)$ having as its components the velocities of each of the selected signals at time $t_D$ and the velocities of each of the selected signals at time $t_D+6$; (b) determining the angle between the vector $F(t_D)$ and a previously-stored template vector; (c) comparing the angle with a threshold angle; and (d) if the angle is less than the threshold angle, categorizing the heartbeat as similar to a heartbeat which corresponds to the template vector.

The present invention is a method which is conveniently illustrated using block diagrams or flow charts to describe the various steps of the inventive method and the embodiments thereof. As used herein, the terms "step", "flow chart element", "process element" or other similar terms may be used to describe the various individual parts of the block diagrams or flow charts. Used as such, there is no intended difference in the meaning of these terms. When an embodiment is illustrated in more than one figure, the term "process portion" and "process" are used herein interchangeably. Specific reference numbering makes such interchangeable usage unambiguous.

The term "velocity" as used herein refers to the rate of change of a signal with respect to time.

The term "within a threshold angle" as used herein refers to an angle being compared with a threshold angle as being less than the threshold angle.

The term "quasi-orthogonal" as used herein refers to the property of a set of ECG signals such that each signal in the set is approximately independent of the other signals in the set. (In an orthogonal set, each signal in the set is fully independent of the other signals in the set.) Graphically, each signal in a two- or three-dimensional quasi-orthogonal set of ECG signals is approximately 90° from the other ECG signals in the set.

BRIEF DESCRIPTION OF THE DRAWINGS

FIG. 4 is a legend for the various terms used in the block diagrams or flow charts of FIGS. 1-3.

FIGS. 6A-6C show representative portions just over 6 seconds long of a set of three digitized ECG signals, sampled at 1,000 samples per second (sps).

FIGS. 7A-7C show the velocities of the digitized ECG signals of FIGS. 6A-6C.

FIGS. 9A-9D show the sum (FIG. 9A) of the absolute velocities of FIGS. 8A-8C, the running maximum value (FIG. 9B) of the sum over contiguous 2-second periods, a threshold T (FIG. 9C) to which the sum is compared during heartbeat detection, and the values of a refractory timer (FIG. 9D) during the time period of FIGS. 6A-6C.

FIG. 10A is a table of detection times of the detected heartbeats during the time period of FIGS. 6A-6C and values of computed velocity and squared vector magnitude of the velocity vector $F(t_D) = \{f_1(t_D), \ldots, f_n(t_D)\}$ generated in the embodiment of FIGS. 1-4 for the selected signals in FIGS. 6A-6C. FIG. 10A also includes three template vectors and their squared vector magnitudes as generated within the example.

FIG. 10B is a table illustrating the computations made during the operation of the inventive method for the time period shown in FIGS. 6A-6C.

FIG. 17A is a table (similar to that of FIG. 10A) which shows detection times of the detected heartbeats during the time period of FIGS. 6A-6C and values of computed velocity and squared vector magnitude of the velocity vector $F(t_D) = \{f_1(t_D), \ldots, f_n(t_D)\}$ generated in the alternative embodiment of FIGS. 15 and 2-4 for the selected signals in FIGS. 6A-6C. FIG. 17A also includes four template vectors and their squared vector magnitudes as generated within this example.

FIG. 17B is a table (similar to that of FIG. 10B) illustrating the computations made during the operation of the alternative embodiment of FIG. 17A of the inventive method for the time period shown in FIGS. 6A-6C.

DETAILED DESCRIPTION OF PREFERRED EMBODIMENTS

Figure 1:
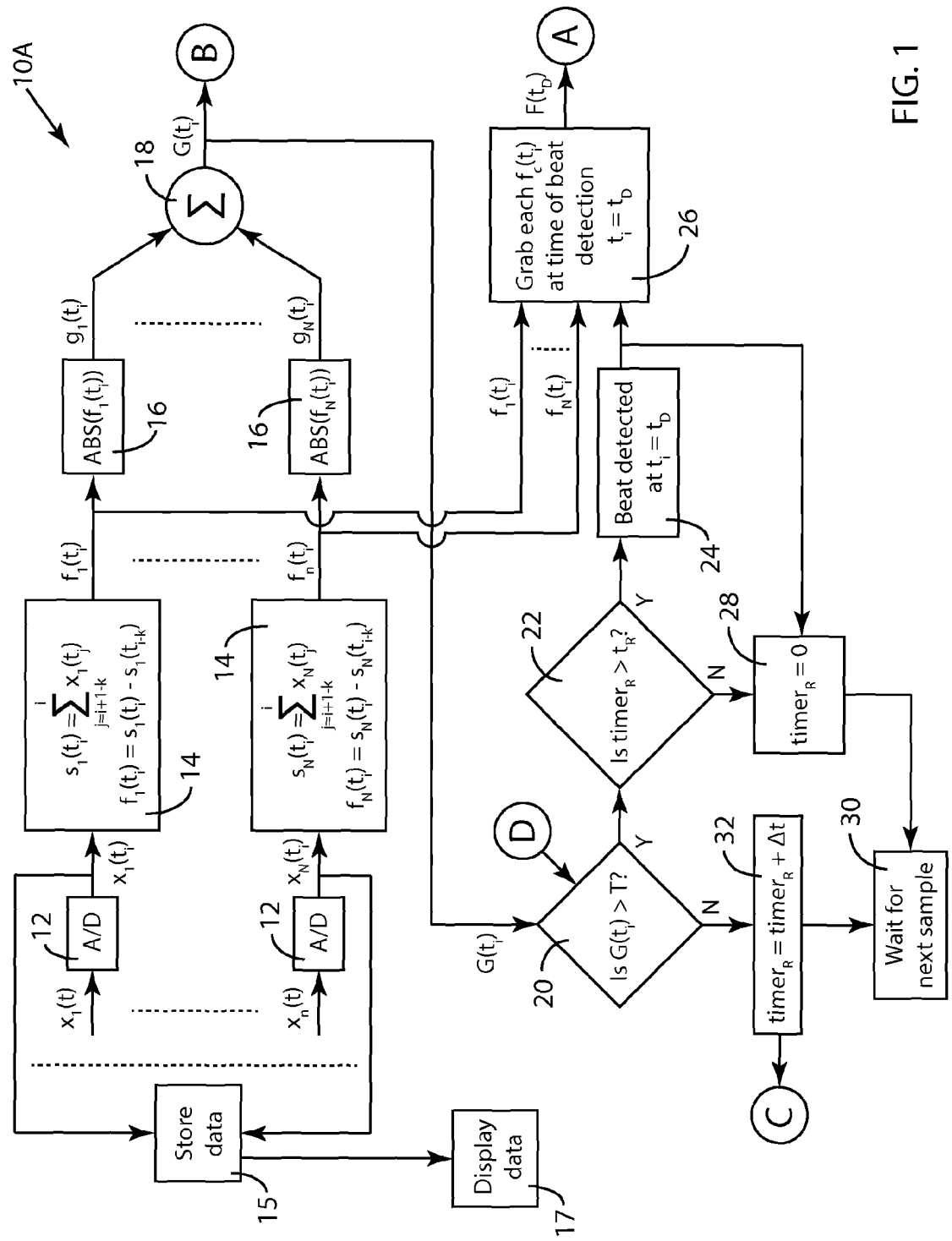
FIG. 1 is a schematic block diagram of a portion of one embodiment of the inventive method for detecting and categorizing heartbeats using two or more ECG signals. The block diagram of FIG. 1 primarily illustrates the portion of such embodiment which filters the ECG signals and detects heartbeats.
Figure 2:
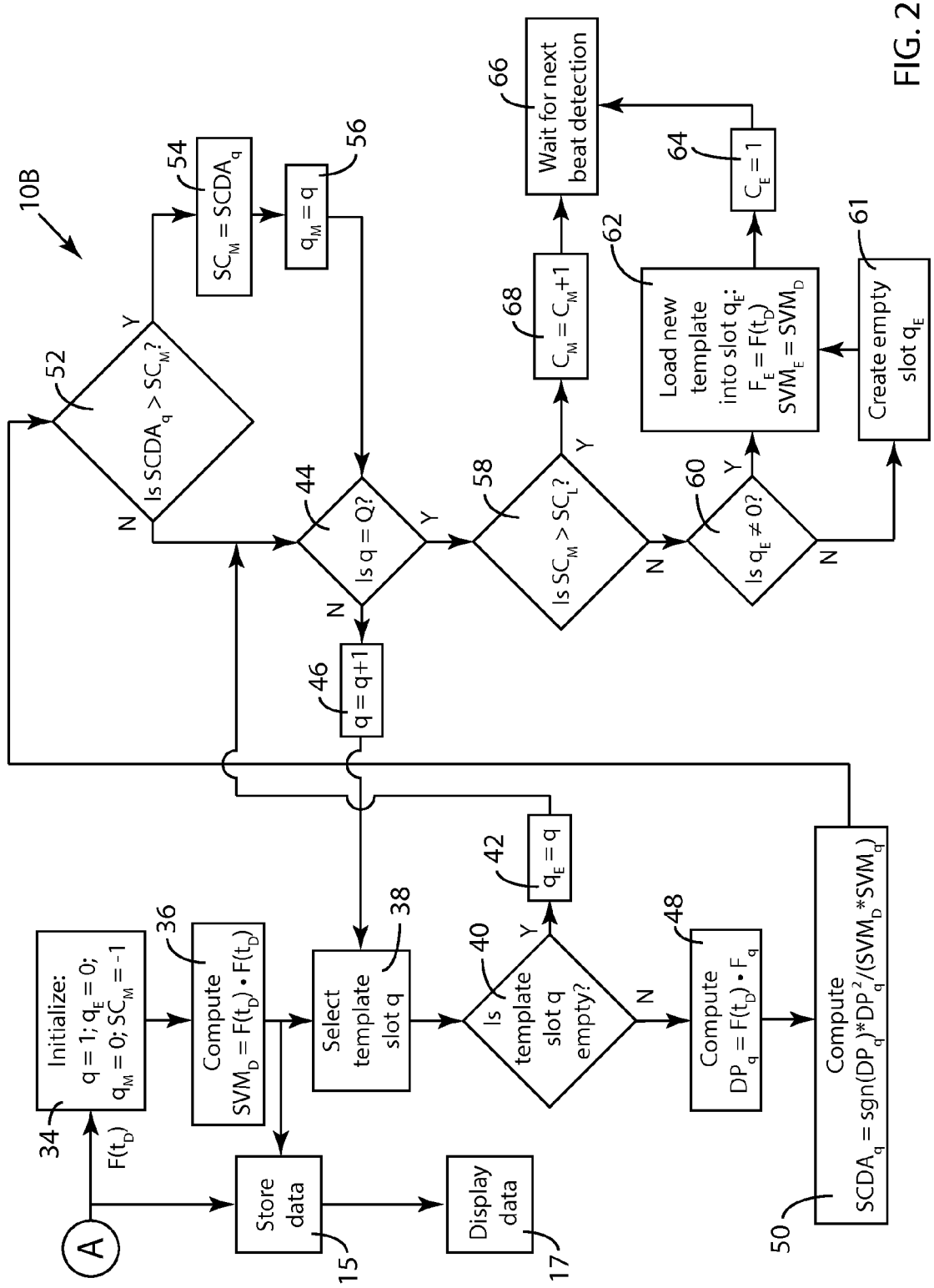
FIG. 2 is a schematic block diagram of another portion of the embodiment partially illustrated in FIG. 1. The block diagram of FIG. 2 primarily illustrates the portion of such embodiment which categorizes the detected heartbeats. This embodiment includes steps to add new templates for comparison with the vector representing a detected heartbeat when the heartbeat is not found to be similar to any of the heartbeats represented by template vectors at the time of heartbeat detection.
Figure 3:
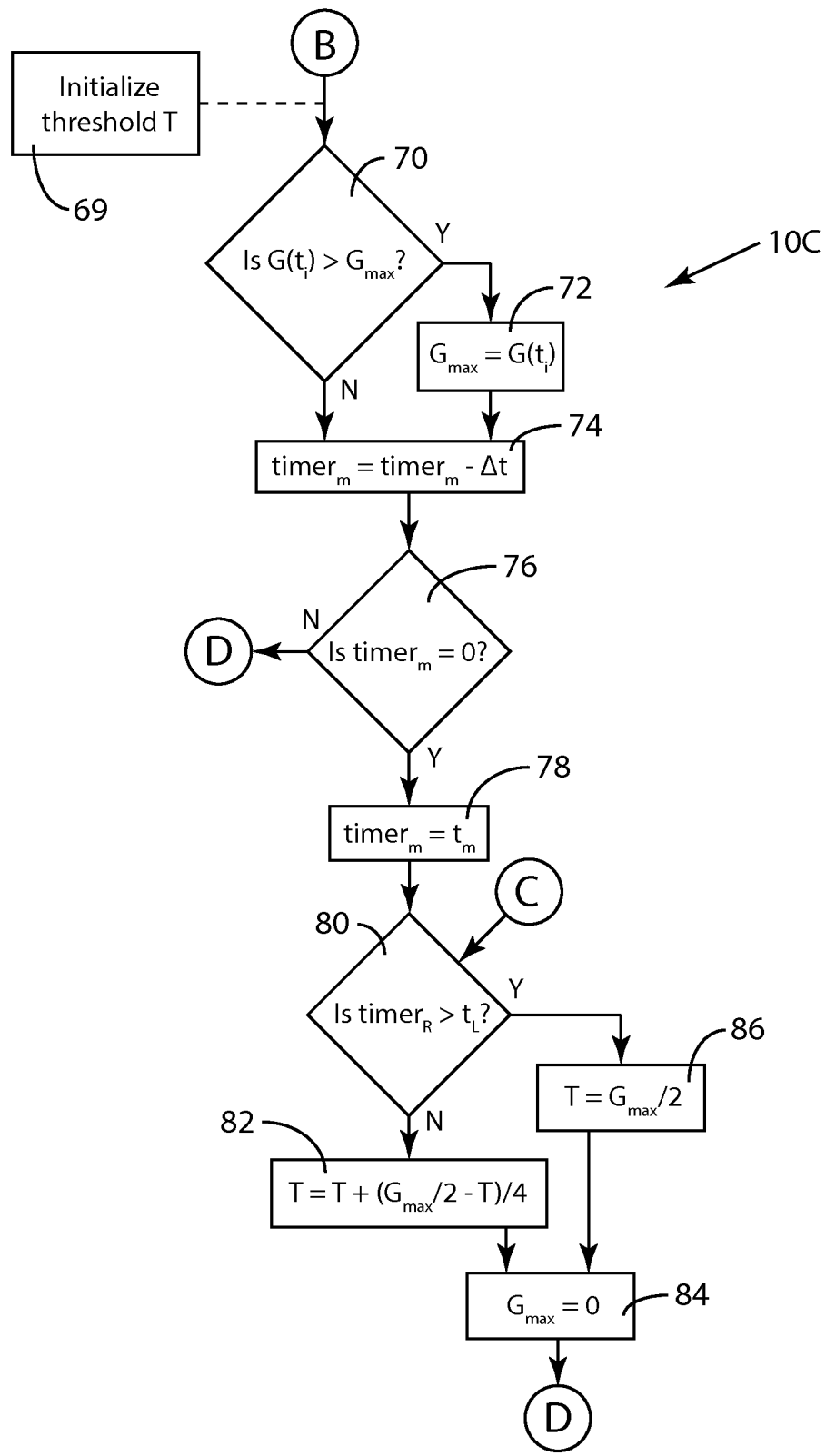
FIG. 3 is a schematic block diagram of yet another portion of the embodiment partially illustrated in FIGS. 1 and 2. The block diagram of FIG. 3 primarily illustrates the portion of such embodiment which sets threshold T used in the embodiment of the inventive method to compare with the sum of the absolute velocities of the plurality of ECG signals, as illustrated in FIG. 1.

FIGS. 1-4 illustrate one embodiment of the inventive method for heartbeat detection using two or more ECG signals. FIGS. 1-3 are schematic block diagram representations of the method. FIG. 4 shows a legend 10E for the various terms used in the embodiment of FIGS. 1-3, giving definitions for the various signals, terms in the equations and preset parameters. The legend also includes a set of typical values for preset parameters which are used within the embodiment.

The block diagram of FIG. 1 is a flow chart of steps illustrating the process portion 10A of this embodiment which filters the ECG signals and detects heartbeats. In FIG. 1, each signal in a set of selected ECG signals $[x_1(t), \ldots, x_N(t)]$ is digitized in analog-to-digital converters (A/D) 12 to form a set of digitized ECG signals $[x_1(t_i), \ldots, x_N(t_i)]$. In this embodiment, A/D converters 12 sample the ECG signals $[x_1(t), \ldots, x_N(t)]$ at a rate of 1,000 sps. For example, $x_1(t_i)$ is the sampled value of $x_1(t)$ at $t=t_i$. The number N of selected ECG signals is 2 or more. Later in the description of this embodiment, the value of N will be 3 for purposes of illustration. Again, N=3 is not intended to be limiting to the scope of the inventive method. (When referring herein to an individual but non-specific signal among sets of N signals, the subscript p may be used.)

Each digitized signal $x_c(t_i)$ in the set of digitized ECG signals $[x_1(t_i), \ldots, x_N(t_i)]$ is filtered in one of N flow chart elements 14 to generate a velocity $f_c(t_i)$ of $x_c(t_i)$ at each sampling time value $t_i$. In this embodiment, filters 14 are first-difference filters, and specifically, boxcar filters with a boxcar width k of 20 samples. As the equations in flow chart elements 14 indicate, velocity $f_c(t_i)$ of $x_c(t_i)$ is the difference between two sums of samples ($s_c(t_i) - s_c(t_{i-k})$), the first sum $s_c(t_i)$ being the sum of the sampled value $x_c(t_i)$ and the previous 19 sampled values of $x_c(t_i)$, and the second sum $s_p(t_{i-k})$ being the sum of the 20 sampled values of $x_c(t_i)$ immediately prior to the samples of the first sum. Since filter 14 is a boxcar filter, it produces some smoothing in the filtered velocity signal $f_c(t_i)$. The wider the boxcars are, the more high frequencies are removed during the filtering process 14. And, the value of velocity $f_c(t_i)$ lags behind the actual time $t_i$, but such lag has no significant effect on heartbeat detection and categorization being processed.

In general, the selected ECG signals may be filtered in a variety of ways to generate values for the velocities $[f_1(t), \ldots, f_N(t)]$ of the selected ECG signals $[x_1(t), \ldots, x_N(t)]$. For example, a more general expression for digital filters includes a set of coefficients multiplying the individual time samples in the summations of flow chart elements 14, such that for ECG signal $x_1(t_i)$, $s_1(t_i) = \Sigma(a_j * x_1(t_{i-j}))$ for $j=0$ to $k-1$, where the values of $a_j$ are a set coefficients. Each sample in the summation is weighted by a coefficient $a_j$. For the boxcar filter example in the embodiment of FIG. 1, all of the $a_j$ are equal to 1. The particular boxcar filter example is not intended to limit the scope of the filter structure in the present invention; other filters made be used to generate the velocities.

The value of boxcar width k=20 is not intended to be limiting; other boxcar widths may be used. For k=20 and a sampling rate of 1,000 sps, the first difference boxcar filter has null points at 0 Hz and integer multiples of 50 Hz, Thus, such a filter has a peak at 19 Hz. With a null at 0 Hz, the filters remove amplifier offsets and low-frequency artifacts. The null at 50 Hz reduces higher-frequency noise.

Each velocity signal $f_c(t_i)$ is further filtered in flow chart element 16 which generates the absolute value $g_c(t_i)$ of $f_c(t_i)$. Then, all N absolute value velocities $[g_1(t_i), \ldots, g_N(t_i)]$ are summed in flow chart element 18 to generate an absolute velocity sum $G(t_i)$ at each sampled instant in time $t_i$.

Velocity sum $G(t_i)$ is an input into a flow chart decision element 20 in which $G(t_i)$ is compared with a threshold T. The value of threshold T is adaptively determined in this embodiment of the inventive method and has a value of about one-half of an expected maximum value of sum $G(t_i)$. More detail of this embodiment of the adaptive determination of threshold T is shown in FIG. 3 and will be described later in this document.

In flow chart element 20, if $G(t_i)$ is greater than threshold T, process 10A proceeds to a flow chart decision element 22, and if $G(t_i)$ is not greater than threshold T, process 10A proceeds to a flow chart element 32 in which a refractory timer (timer$_R$) is incremented by the sampling period $\Delta t$, and process 10A proceeds to flow chart element 30 to wait for the next sampling cycle. In this embodiment, $\Delta t$ is 1 msec since the sampling rate is 1,000 sps.

In decision element 22, if timer$_R$ is greater than a preset refractory period $t_R$, then a heartbeat has been detected at time $t_i = t_D$ as indicated in flow chart element 24, at which point process 10A proceeds to flow chart element 26. After time of detection $t_D$ is set to time $t_i$ in flow chart element 26, timer$_R$ is set to 0 in flow chart element 28 and process 10A proceeds to flow chart element 30 to wait for the next sampling time. In decision element 22, if timer$_R$ is not greater than $t_R$, then timer$_R$ is set to 0 in element 28 and process 10A waits for the next sampling time in element 30.

In flow chart element 26, a vector $F(t_D)$ is formed from each of the velocities $f_c(t_D)$ such that vector $F(t_D) = \{f_1(t_D), \ldots, f_N(t_D)\}$. (As used herein, vector quantities are indicated by the use of curly brackets as in the definition of $F(t_D)$ above. The square bracket notation as used earlier herein, such as the set of digitized ECG signals $[x_1(t_i), \ldots, x_N(t_i)]$, indicates a series of quantities not operated on as a vector.)

Flow chart element 15 in FIG. 1 illustrates that the N digitized selected ECG signals $[x_1(t_i), \ldots, x_N(t_i)]$ are stored within the inventive method. Flow chart element 17 illustrates that the stored data may be displayed to a user during or after the operation of the inventive method. Flow chart elements 15 and 17 also appear in FIGS. 2 and 12 to indicate that data other than as indicated in FIG. 1 may also be stored and displayed within the inventive method. Other data not specifically shown in these figures may also be stored and/or displayed as desired since the inventive method is implemented within a digital computer which easily stores data for later use. Certain interim values can of course be recomputed but for purposes of speed, storing for later use may be preferred. The indications of specific data stored are not intended to be limiting within the scope of the present invention.

FIG. 1 shows four circled letters A through D. These points within the flow chart of FIG. 1 indicate points in process 10A of the embodiment which proceed to similarly-labeled points within either FIG. 2 or FIG. 3. These points of process continuity will be discussed later in the detailed description.

FIG. 2 is a schematic block diagram of another portion of the embodiment partially illustrated in FIG. 1. It is a flow chart of steps illustrating the process portion 10B of the embodiment which categorizes the detected heartbeats.

Referring to FIG. 2, point A indicates that this process portion 10B of the embodiment of the inventive process proceeds from point A of FIG. 1, at which point a heartbeat has been detected at time $t_D$ and vector $F(t_D)$ of velocities has been formed. Heartbeat detection time $t_D$ occurs during the initial portion of a heartbeat, and $F(t_D)$ is a vector quantity which characterizes the detected heartbeat in the remaining steps of the inventive method for the detection of heartbeats.

During the heartbeat categorization portion 10B of this embodiment, the method stores template heartbeats, corresponding template vectors and other related information at least for comparing with a detected heartbeat which has been detected in process portion 10A. Such template vectors are described as being stored in template vector slots (slots), and there are assumed in this embodiment to be Q such slots. The slots are identified as having an index q from 1 to Q. When a heartbeat is categorized as being similar to the template associated with slot q, a heartbeat count $C_q$ is incremented by 1 such that the number of heartbeats in each category is counted.

In FIG. 2, four variables are initialized in flow chart element 34 at the beginning of the categorization of each detected heartbeat. These four variable initializations are: $q=1$; $q_E=0$; $q_M=0$; and $SC_M=-1$. Template index q is set to a starting slot (slot 1), and an empty slot index $q_E$ (indicating that slot $q_M$ is available for a new template vector) is set to point to no slot ($q_E=0$). A slot index $q_M$ is the index of the slot containing the template vector associated with the computed quantity $SC_M$ which is itself set to $-1$ in the initialization steps of flowchart element 34. At the time of initialization 34, no slot is associated with a value of $SC_M$ ($q_M=0$). (The term $SC_M$ will be defined later in this detailed description of FIG. 2.)

In flow chart element 36, a value for $SVM_D$ is computed as the dot product of vector $F(t_D)$ with itself: $SVM_D = F(t_D) \cdot F(t_D)$. $SVM_D$ is herein called the squared vector magnitude of vector $F(t_D)$. The dot product of two vectors X and Y is equal to the product of the magnitude of the each vector times the cosine of the angle $\theta$ between the vectors: $X \cdot Y = |X| * |Y| * \cos \theta$. Thus, the dot product of a vector with itself is the square of the magnitude of that vector, or the squared vector magnitude (SVM). This quantity and other similar quantities are used later in the steps of the inventive method.

In flow chart element 38, a template vector slot having an index value of q is selected for comparison. For each detected heartbeat, the initial value of index q is 1, but as will be seen, method step 38 will "operate" Q times during the categorization of the detected heartbeat represented by vector $F(t_D)$. Flow chart decision element 40 determines if slot q contains a template vector $F_q$. If slot q does not contain a vector (a "Yes" decision in element 40), empty-slot index $q_E$ is set to q in flow chart element 42, and slot index q checked against Q in flow chart decision element 44 to see if any slots remain to be compared with vector $F(t_D)$. If the current value q of the slot index is less than the total number of slots Q, slot index q is incremented in flow chart element 46, and process 10B returns to flow chart element 38 to continue heartbeat categorization. (A "Yes" decision in flow chart element 44 will be discussed later in this detailed description of FIG. 2.)

At flow chart element 40, when a template is found in slot q, template vector $F_q$ and previously-computed $SVM_q$ (computed in element 36 during a previous heartbeat categorization cycle) are available for the comparison of the heartbeat at time $t_D$. Process 10B then proceeds with such comparison by computing a dot product $DP_q = F(t_D) \cdot F_q$ and a quantity $SCDA_q$ in flow chart elements 48 and 50, respectively. $SCDA_q$ is herein called the signed squared cosine difference angle between template vector $F_q$ and vector $F(t_D)$ associated with the detected heartbeat. In flow chart element 50, the computed terms $DP_q$, $SVM_q$ and $SVM_D$ are used to compute $SCDA_q$:

$$SCDA_q = \text{sgn}(DP_q) * DP_q * DP_q / (SVM_D * SVM_q)$$

where the * symbol indicates multiplication. Thus, the magnitude of the quantity $SCDA_q$ is the square of the cosine of the angle $\theta_q$ between vector $F(t_D)$ and vector $F_q$, and the sign of $SCDA_q$ is the sign of the cosine of the angle $\theta_q$. As can be seen from the above expression for $SCDA_q$, $SCDA_q$ is indicative of how closely aligned vector $F(t_D)$ is with template vector $F_q$ or how small the angle between the two vectors is. In this embodiment, the quantity $SCDA_q$ is being used as a computational convenience to find the angle $\theta_q$ without the need for computing square roots and inverse cosines of quantities. Of course, any other algebraic formulations may be used to determine the relative alignment of vectors $F(t_D)$ and $F_q$.

The categorization of a heartbeat is based on the relative alignment of vector $F(t_D)$ with template vectors $F_q$. If two vectors are fully aligned, the angle $\theta_q$ between the two vectors is 0° and cosine of $\theta_q$ is 1. If angle $\theta_q$ is within a preset threshold angle $\theta_L$, the detected heartbeat associated with vector $F(t_D)$ is categorized as being similar to the heartbeat associated with template vector $F_q$. In the embodiment of FIG. 2, the comparison of angle $\theta_q$ with a preset threshold angle $\theta_L$ is done by comparing $SCDA_q$ with a limit value $SC_L$ which defines the magnitude of angle $\theta_q$ such that $F(t_D)$ is in the region of template vector $F_q$. For example, if a preset threshold angle $\theta_L$ of 25° is being used as such a threshold angle, $SC_L = \cos^2(25°)$ or $SC_L \cong 0.8214$.

In the embodiment of FIG. 2, the value of $SC_L$ is the same for each template vector. In other embodiments, the values of $SC_L$ associated with each of the template vectors may differ depending on the features of the various heartbeats associated with the template vectors.

In flow chart elements 52 through 58, categorization process 10B determines for each detected heartbeat (1) what the maximum value of $SCDA_q$ is and (2) whether or not vector $F(t_D)$ is within the threshold angle $\theta_L$ of the template for which $SCDA_q$ is maximum. Process 10B proceeds to flow chart decision element 52 in which the computed value of $SCDA_q$ is compared with the value of the quantity $SC_M$. $SC_M$ is the maximum value of $SCDA_q$ for all values of q for which values of $SCDA_q$ have been computed during the categorization of a detected heartbeat. The highest possible value of $SCDA_q$ is, of course, 1 which indicates that $F(t_D)$ and $F_q$ are precisely aligned with each other (angle $\theta_q = 0°$), and the lowest possible value for $SCDA_q$ is −1 indicating that $F(t_D)$ and $F_q$ are pointing in precisely opposite directions (angle $\theta_q =) 180°$. During initialization at step 34, $SC_M$ was set to −1 so that all larger values of $SCDA_q$ are found as the sequential operations of categorization process 10B proceed.

If in decision element 52 $SCDA_q$ is found to be greater than $SC_M$, $SC_M$ is given the current $SCDA_q$ in flow chart element 54, and $q_M$, the index of the template vector which corresponds to $SC_M$, is given the value of the current index q in flow chart element 56. Process 10B then proceeds to flow chart decision element 44 in which current index q is compared with the total number of template slots Q. If in decision element 52 $SCDA_q$ is found not to be greater than $SC_M$, process 10B also proceeds to flow chart decision element 44.

In flow chart decision element 44 as described above, slot index q is checked against Q to see if any slots remain to be compared with vector $F(t_D)$. If q is not equal to Q, then the value of index q is incremented by 1 in flow chart element 46, and categorization process 10B loops back to flow chart element 38 to begin comparison of vector $F(t_D)$ with another template vector $F_q$. If q=Q in flow chart decision element 44 (i.e., the last template vector has been compared to $F(t_D)$ and $SC_M$ and $q_M$ have been identified for $F(t_D)$), process 10B proceeds to determine whether vector $F(t_D)$ is within preset threshold angle $\theta_L$ of template vector $F_M$ ($F_M$ is $F_q$ for q=$q_M$). This determination is done by comparing $SC_M$ with $SC_L$ (as described above) in flow chart element 58. If $SC_M$ is greater than $SC_L$, then vector $F(t_D)$ is within threshold angle $\theta_L$ of template vector $F_M$, and the count $C_M$ ($C_M$ is $C_q$ for q=$q_M$) of heartbeats in the category defined by $F_M$ is increased by 1 in flow chart element 68.

However, if $SC_M$ is not greater than $SC_L$, then process 10B has found that there is no template vector $F_q$ to which $F(t_D)$ is similar, and in this embodiment, $F(t_D)$ is then set as a new template vector if there is an empty template slot $q_E$ still available. Flow chart element 60 determines if a template slot is available ($q_E \neq 0$). If an empty template slot is available, vector $F(t_D)$ is set as template vector $F_E$ ($F_E$ is $F_q$ for q=$q_E$) as shown in flow chart element 62, and this new template category is given a count $C_E$ of 1 ($C_E$ is $C_q$ for q=$q_E$) in flow chart element 64. After either counting vector $F(t_D)$ in an existing template category (flow chart element 68) or in a newly-created template category (flow chart elements 62 and 64), heartbeat categorization process 10B proceeds to flow chart element 66 in which process 10B waits for the next heartbeat to be detected in process 10A.

If in flow chart decision element 60 no empty template slot is found, an empty template slot is created in flow chart element 61 and categorization process 10B continues to flow chart element 62. The example of FIGS. 6A-13F described in detail below is shown using a value of Q (the maximum number of heartbeat categories or templates) of 8. In general, however, the value of Q may be much larger than 8. Since modern computers operate at very high speeds and have essentially unlimited memory, the delay in performing numerous comparisons in categorization process 10B is insignificant, and setting Q to be quite large has little effect on operation of the method and avoids losing information about heartbeats caused by storing only a limited number of templates.

In the event that Q is not set high enough (an "N" result in flow chart decision element 60) for a patient being monitored and a heartbeat is encountered which requires that a new template be formed, flow chart element 61 may include steps which discard the template corresponding to the category which has the lowest number of counts and which has the longest period of time since the category has increased its count. Several other strategies are possible for the creation of a new empty slot $q_E$ in flow chart element 61 to deal with such a situation, but as mentioned above, setting Q to be large enough to avoid encountering needing to discard a template is a simple approach.

Factors which affect the number of template vectors (heartbeat categories) which may be used are, among other factors, the length of time for which a patient is to be monitored, the amount of patient movement during monitoring, the use of different patient postures during monitoring, and the noise environment affecting the ECG signals. Also affecting the appropriate value of Q is the selected value for $SC_L$. Smaller regions (smaller $\theta_L$) around template vectors mean that Q will likely need to be higher. In general, however, it is expected that for patients having a variety of ectopic heartbeats, the number of categories is still quite limited since the morphology of a heartbeat is determined by its trigger source within the heart, and thus heartbeats of the same morphology result from triggers occurring at the same points in the heart.

Many other logical strategies for filling template slots, assessing angle $\theta$ between vectors, and other parts of the logical flow of the embodiment of FIGS. 1-4 are possible within the scope of the inventive method. For example, the embodiment of FIG. 2 fills template slots beginning with slot Q (Q being the highest slot index) and then fills the highest available empty template slot when another vector is found to be a new template vector. Thus, if any empty slots are available, they will have lower slot index values than any filled template slot. It is not a limitation of this invention that the order in which slots are filled begin with the highest slot number.

FIG. 3 is a schematic block diagram of yet another portion of the embodiment partially illustrated in FIGS. 1 and 2. The block diagram of FIG. 3 is a flow chart of steps illustrating a process portion 10C of the embodiment that sets the threshold T which is compared in flow chart element 20 with sum $G(t_i)$ of the absolute velocities of the plurality of ECG signals, as illustrated in FIG. 1.

Point B in FIG. 3 indicates that this process portion 10C of the embodiment of the inventive process proceeds from point B of FIG. 1. Process 10C uses sum $G(t_i)$ of the absolute velocities of the plurality of ECG signals to adjust threshold T every preset time period of $t_m$ seconds based on $G(t_i)$, refractory timer (timer$_R$) from point C in FIG. 1, and a threshold timer (timer$_m$) running within process 10C. Flow chart element 69 is connected by a dotted line to indicate that it functions only upon start-up to initialize threshold T.

In flow chart decision element 70, the value of $G(t_i)$ is compared with $G_{max}$. $G_{max}$ is the maximum value of $G(t_i)$ during preset time period $t_m$ as determined by flow chart elements 70-78 and 84. ($G_{max}$ is determined during preset time period $t_m$, and if average signal levels drift, the estimate of the expected maximum value in this embodiment also changes due to the preset time period $t_m$ periodically renewing the value of $G_{max}$.) If $G(t_i)$ is greater than $G_{max}$ in decision element 70, $G_{max}$ is updated with a new value, $G(t_i)$ in flow chart element 72 and threshold timer (timer$_m$) is decremented by $\Delta t$ in flow chart element 74. ($\Delta t$ in this embodiment is 1 msec.) If $G(t_i)$ is not found to be a new maximum in decision element 70, then threshold timer (timer$_m$) is decremented by $\Delta t$ in flow chart element 74. Threshold timer (timer$_m$) is checked to see if preset time period $t_m$ has elapsed (timer$_m$=0) in flow chart decision element 76. If timer$_m$ is not equal to 0 in decision element 76, process portion 10C is complete, and threshold T remains at its current value for the next comparison in flow chart element 20 of FIG. 1. Preset time period $t_m$ in the embodiment of FIGS. 1-4 is 2 seconds. Such a value for $t_m$ is not intended to be limiting; other values may be used. Higher values of $t_m$ cause the rate at which threshold T to be adjusted but also reduce the risk that no heartbeat occurs within period $t_m$.

If preset time period $t_m$ has elapsed (timer$_m$=0) in decision element 76, threshold timer (timer$_m$) is reset to preset time period $t_m$ in flow chart element 78, and process portion 10C proceeds to adjust threshold T in flow chart elements 80, 82 and 86. In flow chart decision element 80, the value of refractory timer (timer$_R$) (from point C of FIG. 1) is compared with a preset detection failure time limit $t_L$.

The refractory timer (designated timer$_R$) measures the elapsed time since the last detected heartbeat. Two preset threshold time values are associated with refractory timer$_R$, preset refractory period $t_R$ and preset detection failure time limit $t_L$. These two threshold values provide two different functions. Preset refractory period $t_R$ serves to prevent false positive detections from occurring too soon after a heartbeat is detected. Preset detection failure time limit $t_L$ serves to monitor the overall detection process in the event that the detection process is failing (e.g., threshold T must be adjusted by a large amount because the signals have changed dramatically).

If timer$_R$ is greater than preset detection failure time limit $t_L$, threshold T is set to $G_{max}/2$ in flow chart element 86. If timer$_R$ is not greater than preset detection failure time limit $t_L$, threshold T is adjusted to $T=T+(G_{max}/2-T)/4$ where the values of T on the right side of the equation (and in element 82 in FIG. 2) represent the previous value of the threshold T. This equation is written in the form as used in computer coding, and such form is well-known by those skilled in the art of computer programming. After new values for threshold T have been set in flow chart elements 82 or 86, $G_{max}$ is reset to 0 in flow chart element 84 since timer$_m$ has been reset in element 78 and the new value for threshold T is provided to process portion 10A in FIG. 1, point D. Preset detection failure time limit $t_L$ is 5 seconds in the embodiment of FIGS. 1-4. Such a value for $t_L$ is not intended to be limiting to the scope of the invention; other values may be used.

Figure 5:
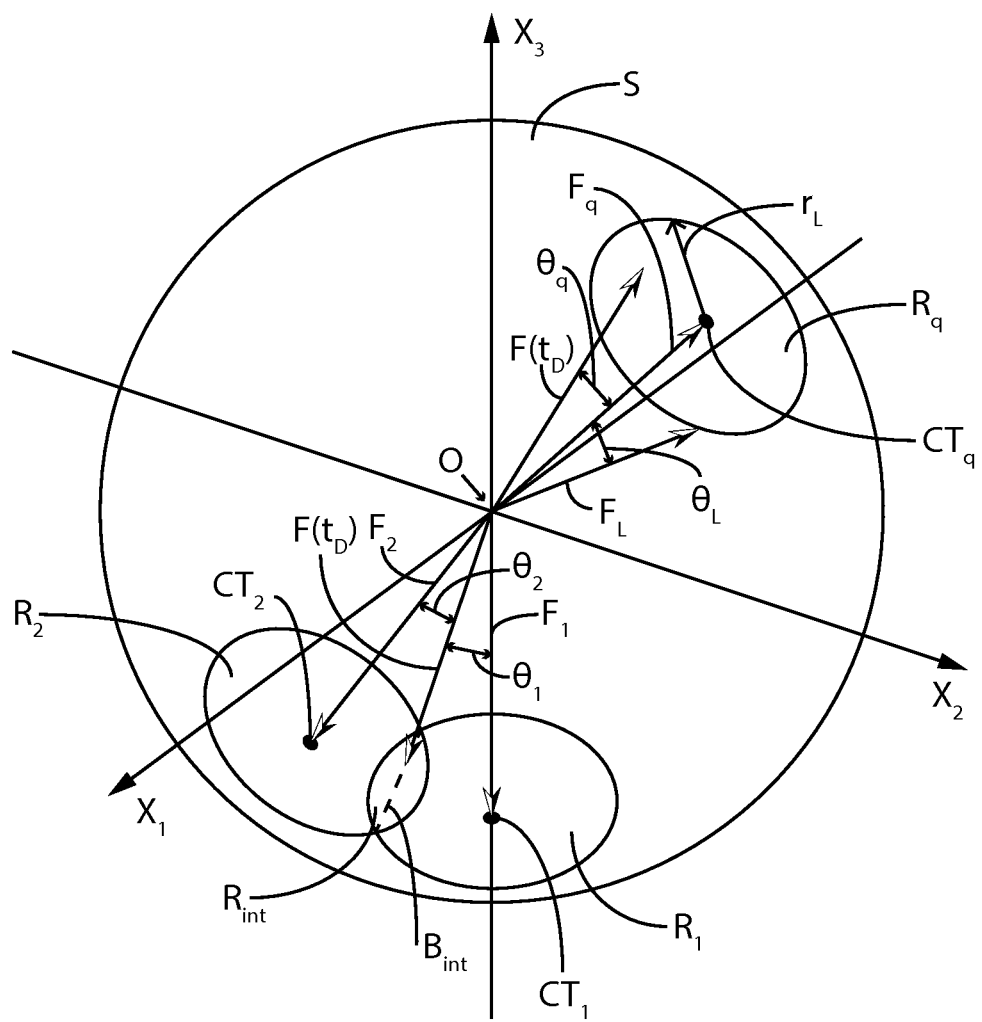
FIG. 5 is a drawing depicting a vector 3-space to illustrate the vector relationships employed in the inventive method.
Figure 8A:
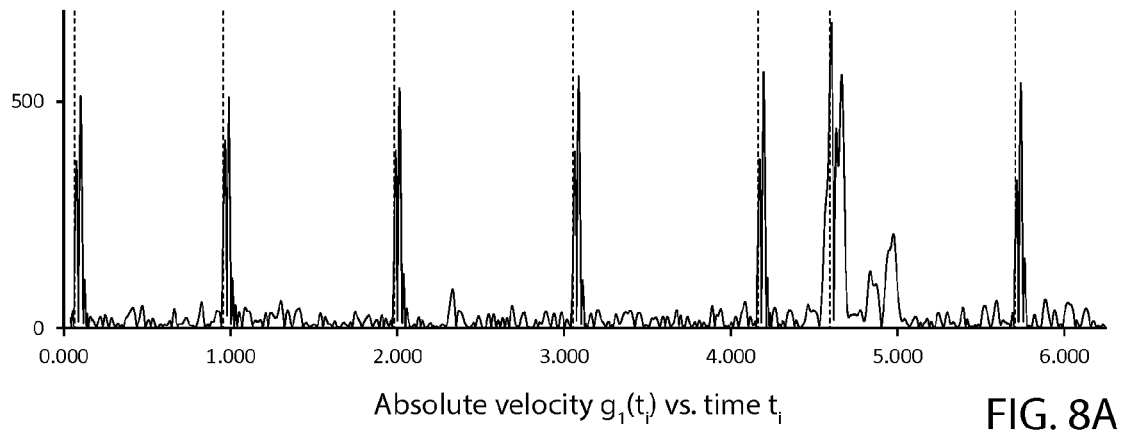
FIGS. 8A-8C show the absolute velocities of the digitized ECG signals of FIGS. 6A-6C.
Figure 8B:
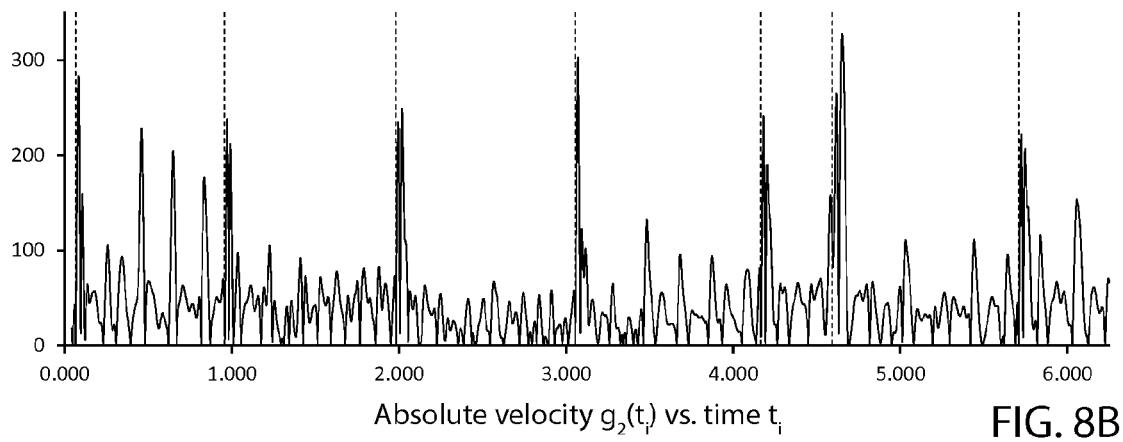
Figure 8C:
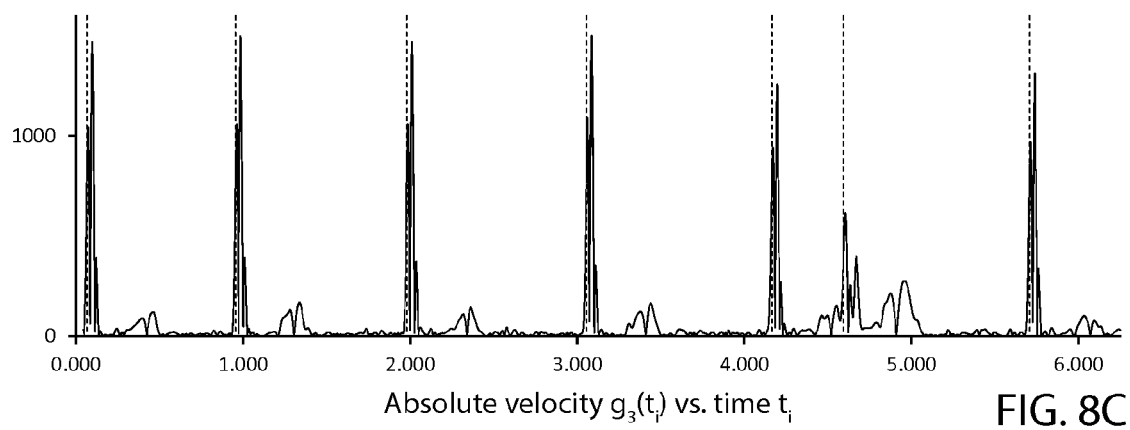

FIG. 5 is a drawing depicting an N=3 vector space to illustrate the vector relationships employed in the inventive method. (Spaces for N>3 are of course not able to be drawn, but the concepts illustrated in FIG. 5 apply to methods employing greater than three selected ECG signals.) The elements of the drawing of FIG. 5 are employed as a means of illustration. For example, sphere S has no significance within the inventive method and is used here as a convenient way to illustrate a region $R_q$ subtended by a category represented by vector template $F_q$. Sphere S is centered around the origin O of a set of axes $[X_1, X_2, X_3]$ representing three directions in the 3-space and corresponding to three selected ECG signals. In FIG. 5, these axes are shown as an orthogonal set, but the selected ECG signals may not be "orthogonal" in a strict mathematical sense for the inventive method to be employed.

Drawn on the surface of sphere S is region $R_q$ which is centered around template vector $F_q$. Region $R_q$ has a radius of $r_L$ which results from the preset threshold angle $\theta_L$ and limit value $SC_L$ of $SCDA_q$ as described above. (In the embodiment of FIGS. 1-4, $\theta_L$=25°.) A vector $F_L$ is shown to illustrate one vector of a set of template vectors which are at the threshold limit angle $\theta_L$ for template vector $F_q$. A vector $F(t_D)$ representing a detected heartbeat at time $t_D$ which may be categorized as being in heartbeat category q since its angle $\theta_q$ is less than $\theta_L$. This heartbeat would be categorized as belonging to category q if its value of $SCDA_q$ was the maximum value $SC_M$ among all values of $SCDA_q$ as in the embodiment of FIGS. 1-4. FIG. 5 also illustrates this portion of the embodiment. At the lower portion of sphere S are two intersecting region $R_1$ and $R_2$ associated with template vectors $F_1$ and $F_2$, respectively. (The fact that these two regions are shown nearly 180° from region $R_q$ is unimportant. $R_1$ and $R_2$ are used only for illustration and are not related in any way to $R_q$.) As shown, it is possible that template vectors may have regions which overlap. In FIG. 5, this region of overlap is called $R_{int}$, and a boundary line $B_{int}$ marks the line along which the angles $\theta_1$ and $\theta_2$ between a heartbeat vector $F(t_D)$ ending along line $B_{int}$ are equal. With the precision of modern computers, the likelihood of a heartbeat vector ending precisely along line $B_{int}$ is extremely small, and if it occurs, placing $F(t_D)$ in either one of the heartbeat categories is an acceptable strategy. All other heartbeat vectors $F(t_D)$ ending in $R_{int}$ are categorized according to which angle $\theta_1$ and $\theta_2$ is the smallest, as set forth in the categorization process of FIG. 2.

FIGS. 6A-11D present an example of the operation of the embodiment of FIGS. 1-4. FIGS. 6A-6C show representative portions just over 6 seconds long of a set of three digitized ECG signals $[x_1(t_i), x_2(t_i), x_3(t_i)]$, sampled at 1,000 sps by A/D converters 12 (FIG. 1). (The precision of the digitized data in this example is 1 microvolt.) In the example, $x_1(t_i)$ is a digitized signal from an ECG standard lead II, $x_2(t_i)$ is a digitized signal from an ECG standard lead $V_1$, and $x_3(t_i)$ is a digitized signal from an ECG standard lead $V_5$. Over the same time period as in FIGS. 6A-6C, FIGS. 7A-7C show computed velocities $[f_1(t_i), f_2(t_i), f_3(t_i)]$ of the digitized ECG signals in FIGS. 6A-6C as computed in filters 14 in FIG. 1, and FIGS. 8A-8C show the absolute velocities $[g_1(t_i), g_2(t_i), g_3(t_i)]$ of the digitized ECG signals of FIGS. 6A-6C as generated in flow chart elements 16 in FIG. 1.

FIGS. 9A-9D show the sum $G(t_i)$ (FIG. 9A) of these absolute velocities, the running maximum value $G_{max}$ (FIG. 9B) of sum $G(t_i)$ over contiguous 2-second periods ($t_m$=2 seconds), threshold T (FIG. 9C) to which sum $G(t_i)$ is compared in flow chart element 20 during heartbeat detection, and the values of the refractory timer (timer$_R$) (FIG. 9D) during the time period of FIGS. 6A-6C. Threshold T is initialized in flow chart element 69 (see FIG. 3) to a value of 1000.

Each of FIGS. 6A-9D also show, with dotted vertical lines, the seven detection times $t_D$ as determined in the ECG signal data of the example. The dotted lines 1-7 indicate heartbeat detection times for heartbeats #1-#7, respectively. (Heartbeat reference numbers #1-#7 and heartbeat detection times 1-7 are only shown in FIG. 6A to reduce clutter in the figures. Each such figure is scaled identically so that heartbeats and detection times are easily identified.) In the example, heartbeats are detected at 0.066 seconds, 0.954 seconds, 1.980 seconds, 3.054 seconds, 4.165 seconds, 4.593 seconds, and 5.708 seconds. (These times are relative to the time axis origin chosen for the example and are not actual run times in the ECG data. The 6.25-second time period was simply chosen for this illustration of the inventive method.)

The characteristics of the ECG data in this example are those of the ECG of an atrial flutter patient, and the rapid oscillations particularly evident in $x_2(t_i)$ (lead $V_1$) are not signal noise. These oscillations are referred to as "flutter waves."

FIG. 10A shows a table of detection times of the seven detected heartbeats during the time period of FIGS. 6A-6C and values of computed velocity and squared vector magnitudes of the velocity vector $F(t_D)=\{f_1(t_D), \ldots, f_n(t_D)\}$ generated in the embodiment of FIGS. 1-4 for the selected signals in FIGS. 6A-6C. FIG. 10A also includes three template vectors and their squared vector magnitudes $SVM_D$ as generated within the example. (In this example, the velocities are in units of 62.5 microvolts/second. Thus for example, $f_1(0.066)=186$ equates to 11.625 millivolts per second from 186*62.5=11,625.)

FIG. 10B is a table illustrating the computations made during the operation of the inventive method for the time period shown in FIGS. 6A-6C. Each of the rows of the table of FIG. 10B correspond to the detection time $t_D$ as indicated by the detected heartbeat number in the table of FIG. 10A. Thus, for detected heartbeat #1 at $t_D$=0.066 seconds and the associated heartbeat vector $F(t_D)$ and $SVM_D$, $DP_8$, the dot product of $F(t_D)$ with template vector $F_8$, is −200100, the squared cosine difference angle $SCDA_8$ is −0.1517, and the corresponding angle $\theta_8$ is 112.92°. Similar computations are seen in the table of FIG. 10B for comparisons of the heartbeat vectors #2-#7 with the template vectors as appropriate. In the example, a value for the limit of $SCDA_q$ ($SC_L$) of 0.8214 has been used, corresponding to a threshold angle $\theta_L$ of 25°. (For threshold angle $\theta_L$ of 25°, $SC_L$=) $\cos^2(25°)$ or $SC_L \approx 0.8214$.)

For purposes of illustration, template vector $F_8$ shown in FIG. 10A has been assumed to have been generated by a heartbeat previous to the time period of the ECG data of FIGS. 6A-6C. Since the comparison of heartbeat #1 and template vector $F_8$ results in $SCDA_8$=−0.1517 ($\theta_8$ 113°), heartbeat #1 is not categorized as similar to the heartbeat which generated template vector $F_8$ and thus a new template vector $F_7$ is created.

Heartbeats #2 through #5 and #7 each are similar to heartbeat #1 as represented by template vector $F_7$ and are thus categorized. As seen in the table of FIG. 10B, heartbeat #6 is dissimilar to both of the heartbeats represented by template vectors $F_8$ and $F_7$ and thus a new template vector $F_6$ is created from heartbeat #6.

Figure 11A:
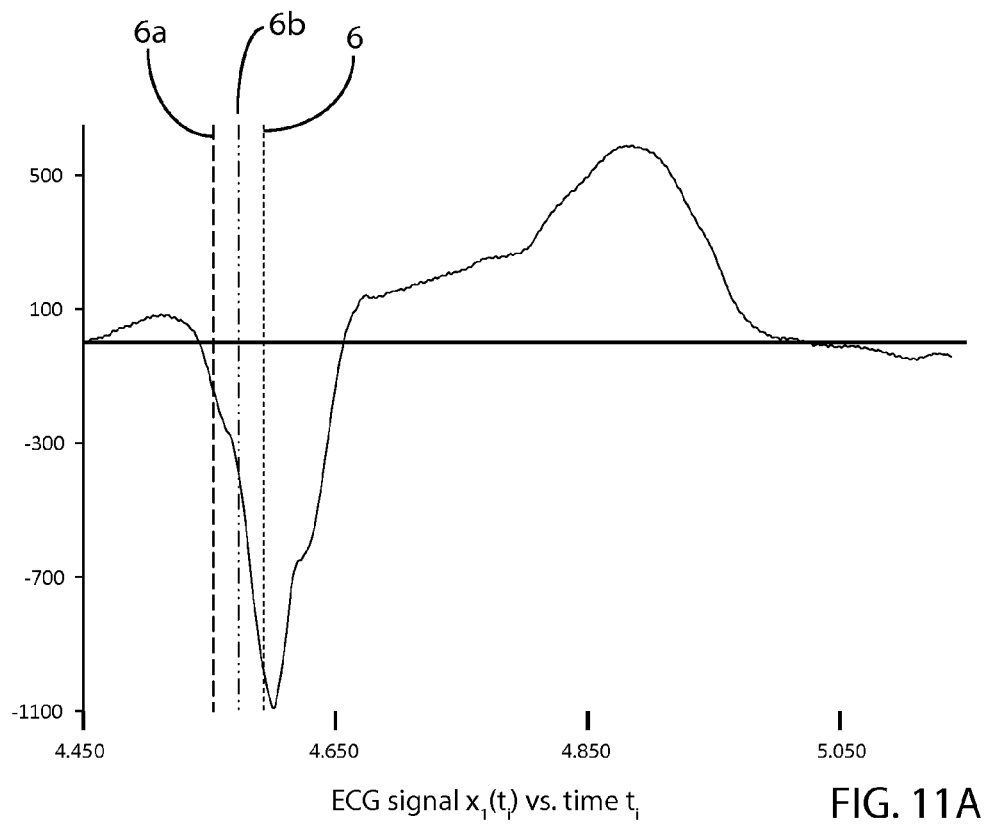
FIGS. 11A-11C show a portion of the ECG signals of FIGS. 6A-6C which include a single detected heartbeat.
Figure 11B:
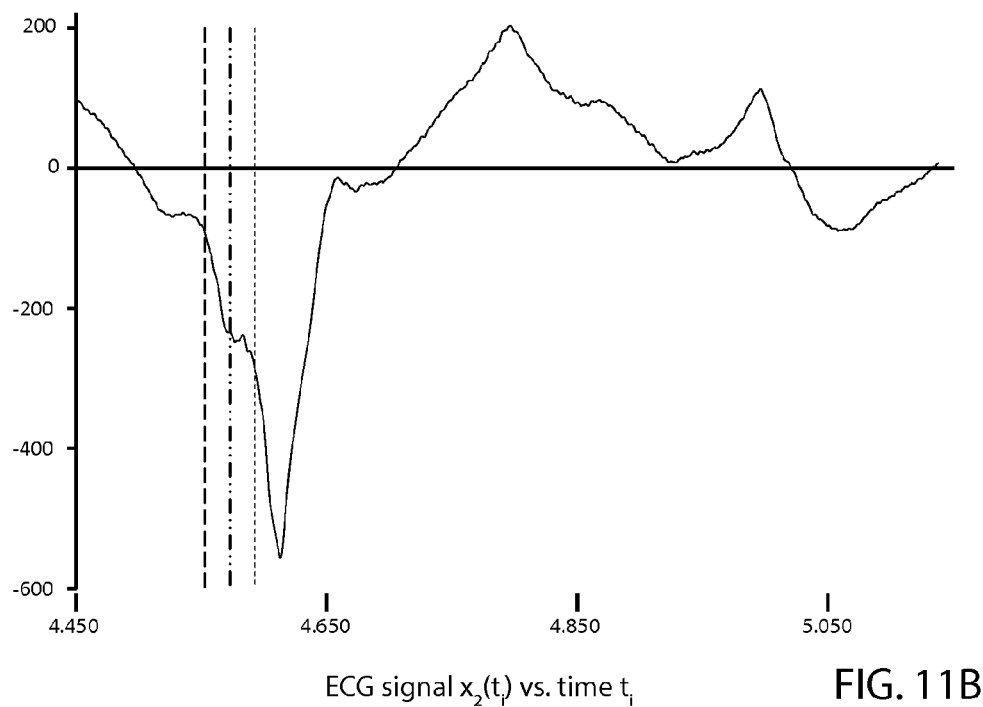
Figure 11C:
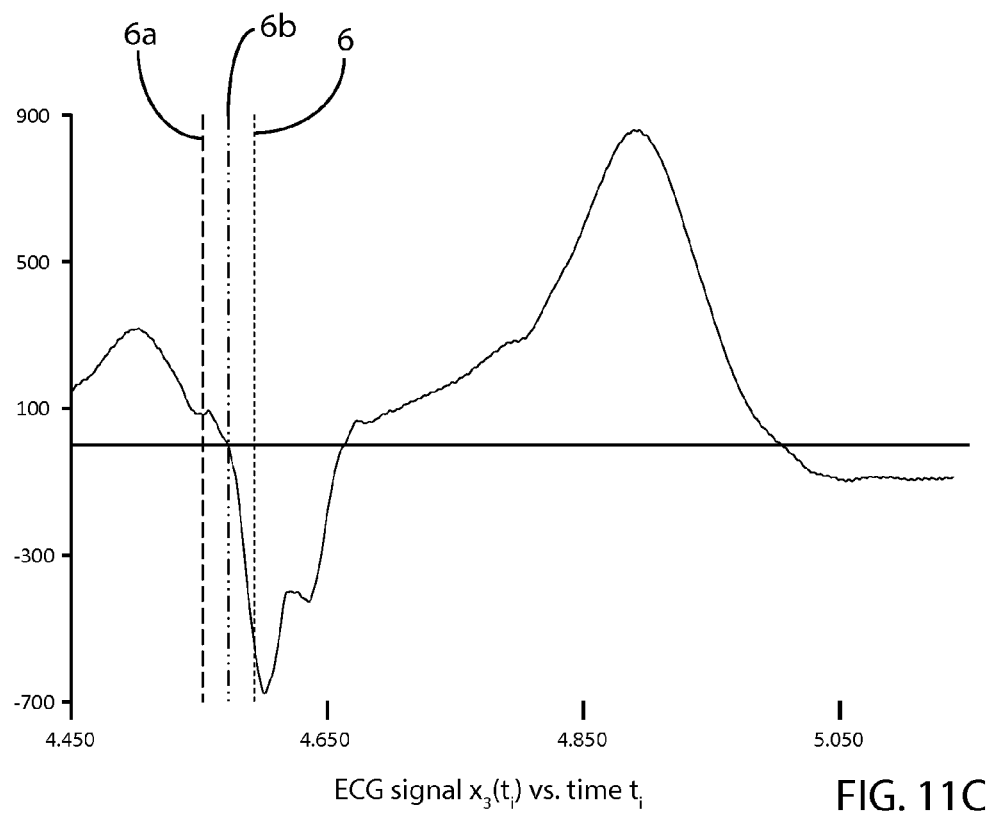
Figure 11D:
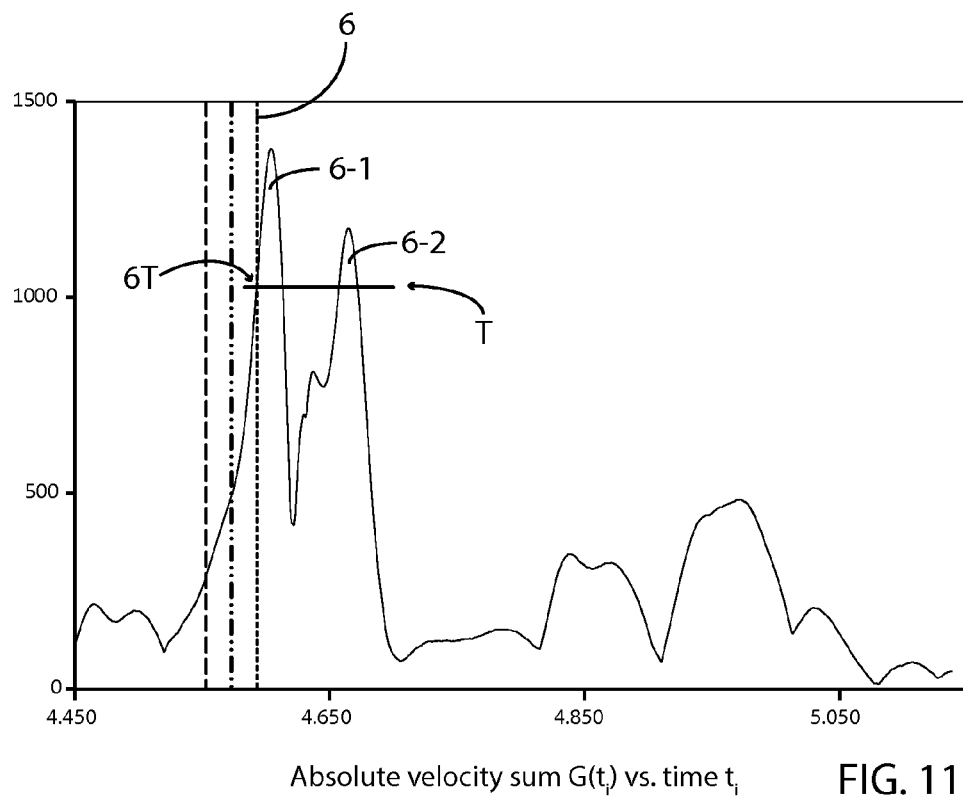
FIG. 11D shows the sum of the absolute velocities for the ECG signals of FIGS. 11A-11C.

Heartbeat #6 detected at 4.953 seconds is a premature ventricular contraction (PVC), and this beat is shown in further detail in FIGS. 11A-11D. FIGS. 11A-11C show the portion of the ECG signals of FIGS. 6A-6C which include single detected heartbeat #6. FIG. 11D shows the sum of the absolute velocities for the ECG signals of FIGS. 11A-11C. In FIGS. 11A-11D, detection time $t_D$=4.593 seconds is indicated by vertical dotted line 6 as in previous FIGS. 6A-9D. (Absolute velocity sum $G(t_i)$ intersects threshold T at $t_D$=4.593 seconds, at intersection 6T, and intersection 6T is marked by vertical dotted line 6.) In addition, two other vertical lines with different dotted-line patterns are shown. Vertical line 6a is located at $t_i$=4.553 seconds, and vertical line 6b is located at $t_i$=4.573 seconds. (Vertical lines 6, 6a and 6b are only labeled in FIGS. 11A and 11C to reduce clutter in the figures.)

The time periods between line 6 and line 6b and between line 6b and line 6a represent the spans of the two boxcars of filters 14 (FIG. 1) which are used in this example to determine velocities $[f_1(t_i), f_2(t_i), f_3(t_i)]$ of the three selected, digitized ECG signals $[x_1(t_i), x_2(t_i), x_3(t_i)]$. Based on this embodiment by which velocities $[f_1(t_i), f_2(t_i), f_3(t_i)]$ are determined, the values of the velocity components which are computed are delayed 20 msec from the "actual" velocities of the ECG signals. In other words, the characteristics of the signal velocities by which the inventive method detects a heartbeat occur very early in the period of a heartbeat. In the case of heartbeat #6 in FIGS. 11A-11D, the features of the signals as they are at $t_i$=4.573 seconds (line 6b) are such that heartbeat

6 is detected. Note that detection occurs at $t_D$=4.593 seconds, not 4.573 seconds, due to the operation of the embodiment of FIGS. 1-4, but the physical signals being processed reach a state at $t_i$=4.573 seconds by which not only is a heartbeat detected but is able to be categorized with such information from early in the period of the heartbeat.

Referring to FIG. 11D which shows the sum $G(t_i)$ of absolute velocities [$g_1(t_i)$, $g_2(t_i)$, $g_3(t_i)$] for the PVC (heartbeat #6), a second peak 6-2 in $G(t_i)$ occurs after a first peak 6-1. There are numerous values of $G(t_i)$ within peaks 6-1 and 6-2 which have values above threshold T, but each of these points occurs at a time well below preset refractory period $t_R$ of 120 msec. Along $G(t_i)$, the final point within peak 6-2 which is above threshold T occurs at t=4.671 seconds, 78 msec after the heartbeat detection at $t_D$=4.593 seconds. As described above, the main function of preset refractory period $t_R$ is to prevent false positive detections from occurring too soon after a detection.

Figure 12:
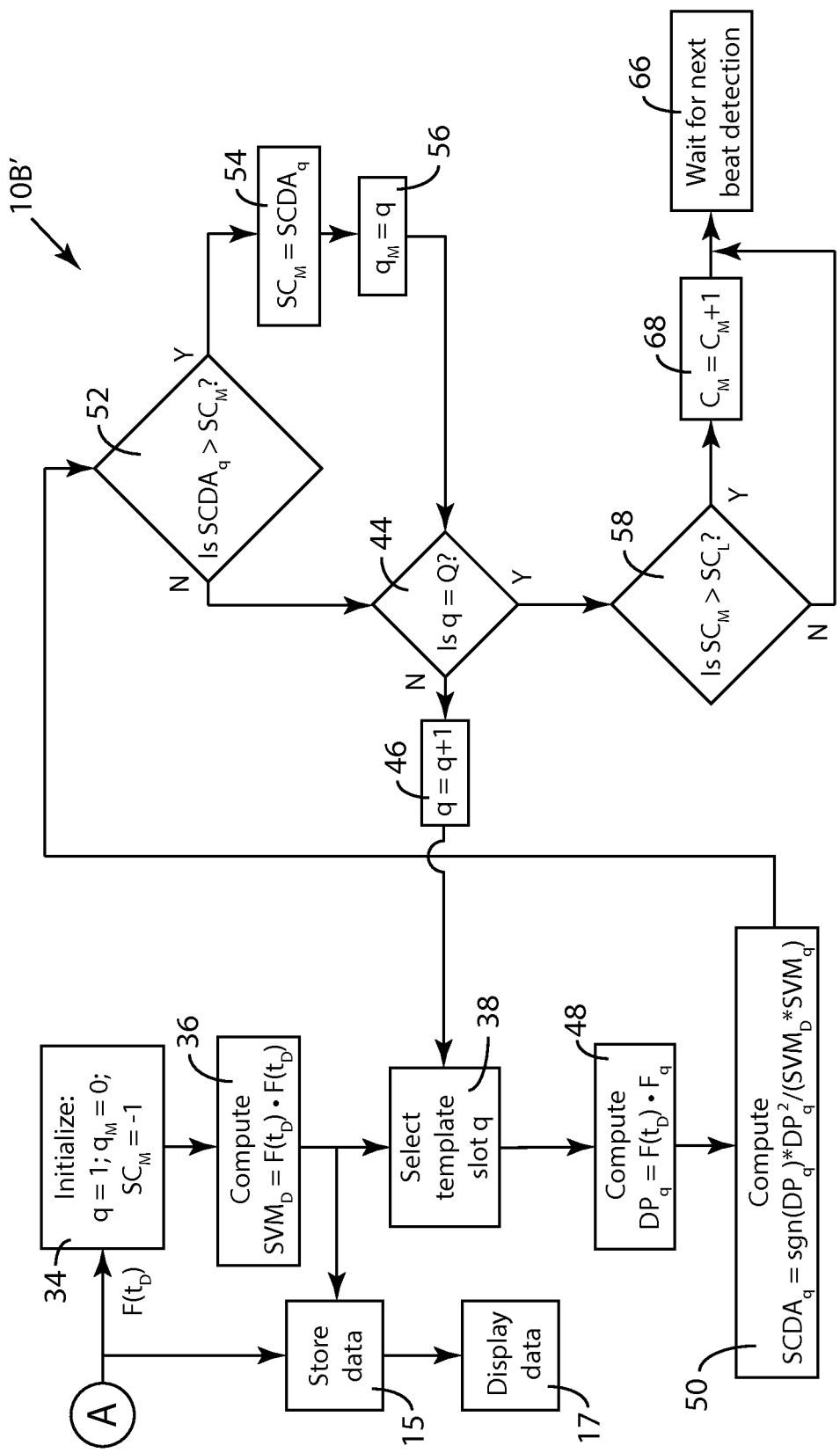
FIG. 12 is a schematic block diagram of an alternative embodiment of the heartbeat categorization portion of the inventive method for heartbeat detection.

FIG. 12 is a schematic block diagram of an alternative embodiment 10B' of the heartbeat categorization portion of the inventive method for heartbeat detection. Alternative embodiment portion 10B' replaces portion 10B of FIG. 2 and is combined with FIGS. 1 and 3-4 to form a complete alternative embodiment of the inventive method. The block diagram of FIG. 12 illustrates a process in which the template vectors to be compared with the vectors representing detected heartbeats are all preset vectors.

Comparing FIG. 12 with FIG. 2, alternative embodiment 10B' does not require the determination of empty template slot $q_E$ which occurs in flow chart decision element 40 and flow chart element 42. Further, the functions of adding a new template vector which occur in flow chart decision elements 60 and 61, and flow chart elements 62 and 64 are also not required. Alternative embodiment 10B' may also be modified to allow preset template vectors to be replaced (as in FIG. 2) if one or more of the preset vectors are found not to be useful during a monitoring procedure.

FIGS. 1-4 also represent an embodiment in which only a portion of the template vectors to be compared with the vectors representing detected heartbeats are preset vectors.

Figure 13B:
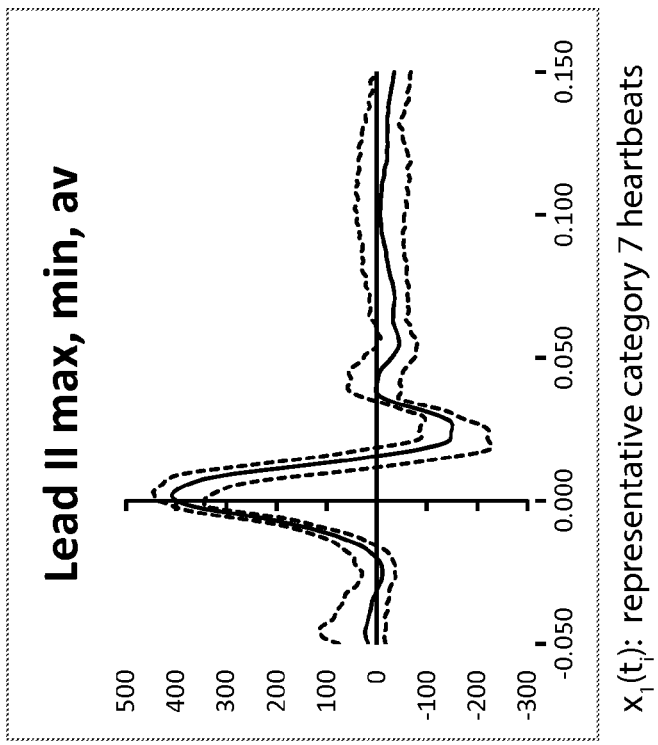
FIG. 13B shows, for the same time period as in FIG. 13A, the maximum, minimum and average values of $x_1(t_i)$.
Figure 13A:
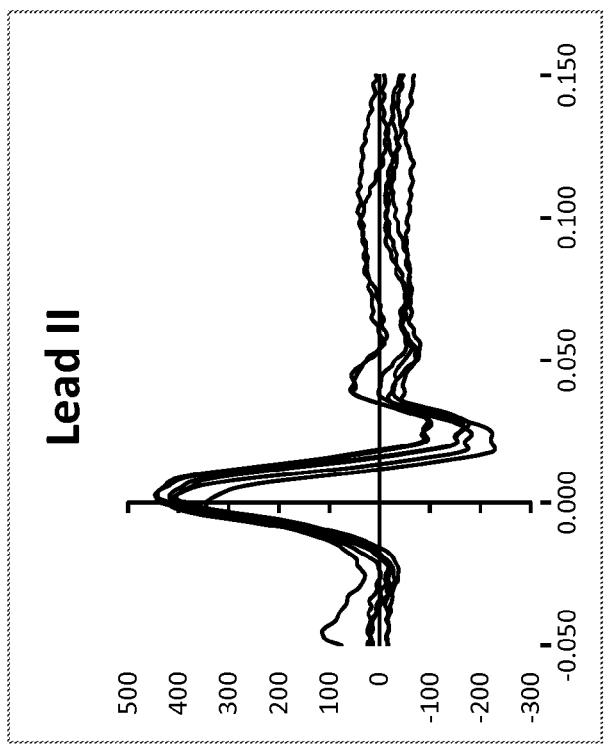
FIG. 13A shows the $x_1(t_i)$ signals for each heartbeat in the example of FIGS. 6A-10B which was detected and categorized as belonging to heartbeat category 7, with each detection time $t_D$ aligned at $t_i=0$ on the plot.
Figure 13D:
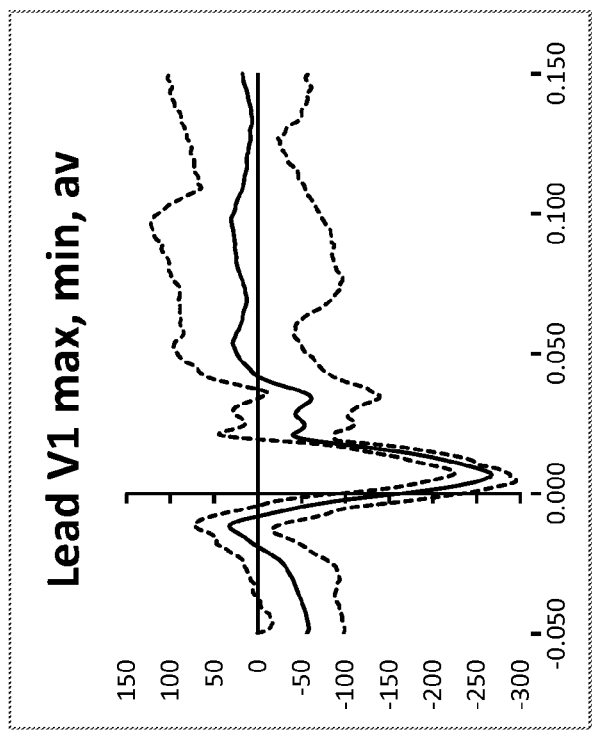
FIG. 13D shows, for the same time period as in FIG. 13C, the maximum, minimum and average values of $x_2(t_i)$.
Figure 13C:
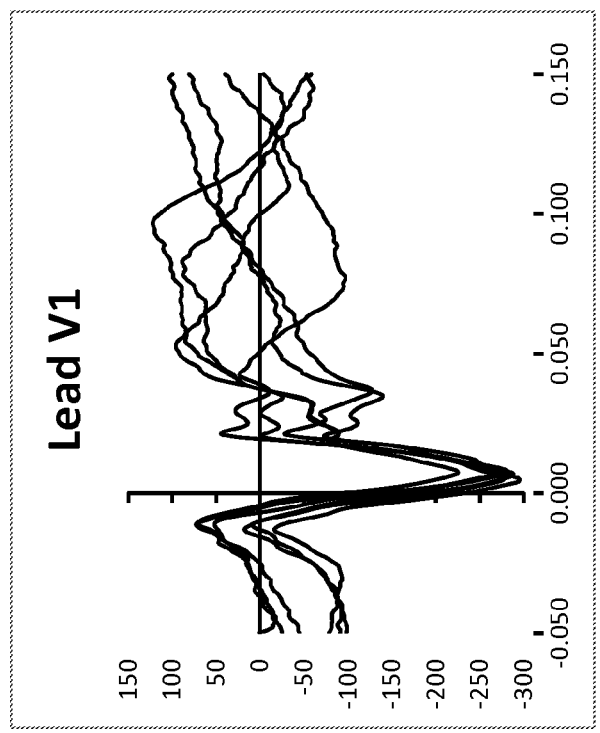
FIG. 13C shows the $x_2(t_i)$ signals for each heartbeat in the example of FIGS. 6A-10B which was detected and categorized as belonging to heartbeat category 7, with each detection time $t_D$ aligned at $t_i=0$ on the plot.
Figure 13F:
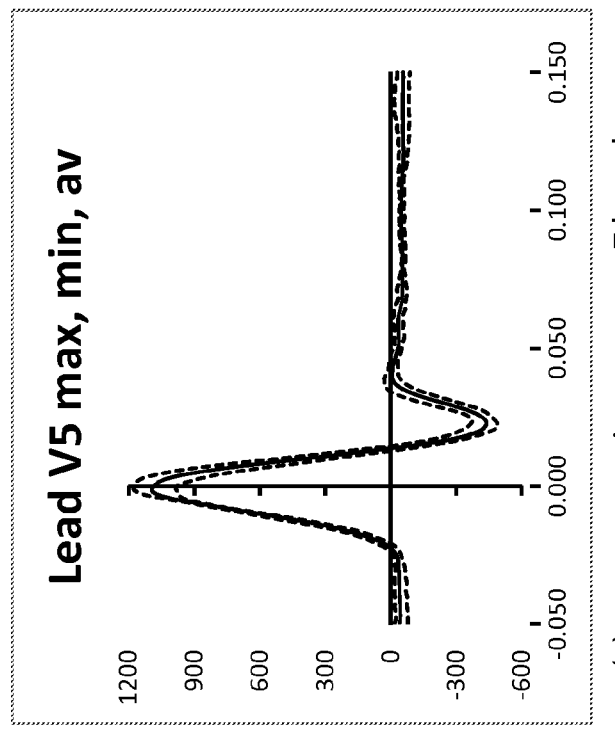
FIG. 13F shows, for the same time period as in FIG. 13E, the maximum, minimum and average values of $x_3(t_i)$.
Figure 13E:
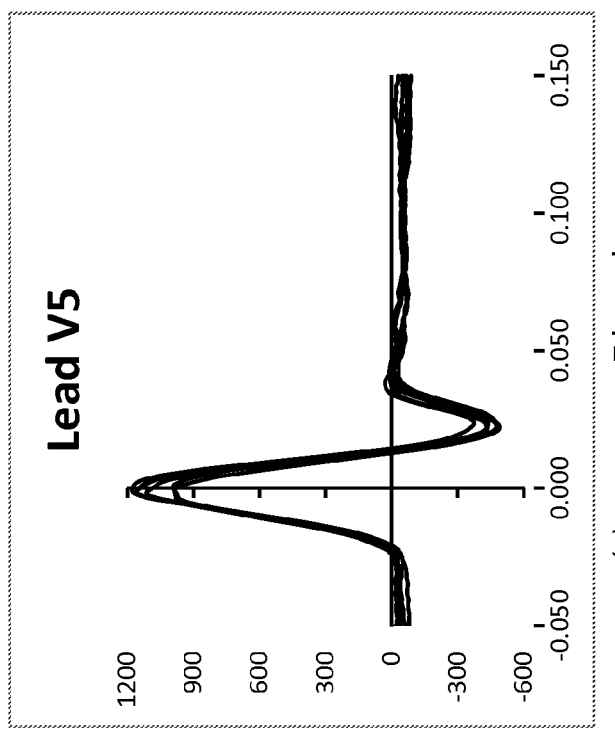
FIG. 13E shows the $x_3(t_i)$ signals for each heartbeat in the example of FIGS. 6A-10B which was detected and categorized as belonging to heartbeat category 7, with each detection time $t_D$ aligned at $t_i=0$ on the plot.

FIG. 13A shows the $x_1(t_i)$ signals for each heartbeat in the example of FIGS. 6A-10B which was detected and categorized as belonging to heartbeat category 7, with each detection time $t_D$ aligned at $t_i$=0 on the plot. FIG. 13B shows, for the same time period as in FIG. 13A, the maximum, minimum and average values of $x_1(t_i)$. The pairs of figures (FIGS. 13C-13D and 13E-13F) in similar fashion show the $x_2(t_i)$ and $x_3(t_i)$ signals, respectively. A user of the inventive method may wish to view the results of the method, such as on a computer display. One possible way in which results may be displayed include the superimposed traces of the individual selected ECG signals as illustrated in FIGS. 13A, 13C and 13E. By such a display the user can confirm that the heartbeats in a category indeed have similar morphology. A user may also confirm that a category represents a particular heartbeat morphology of interest. The specific morphology may be seen more clearly in the display of information such as is shown in FIGS. 13B, 13D and 13F. In such figures, an envelope containing all of the heartbeats in a category is shown by displaying the maximum and minimum values of the selected ECG signals as a function of time $t_i$ of all heartbeats in a category. This envelope is indicated by the dotted-line traces of such figures. This envelope is one such way of displaying a representative heartbeat.

Another way of showing a heartbeat representative of a category is to compute and display the average of all heartbeats in a category as a function time $t_i$. Such information is shown as the solid-line trace in FIGS. 13B, 13D and 13F. Other possible representative heartbeats are possible such as computing and displaying the median as a function of time $t_i$.

Figure 14:
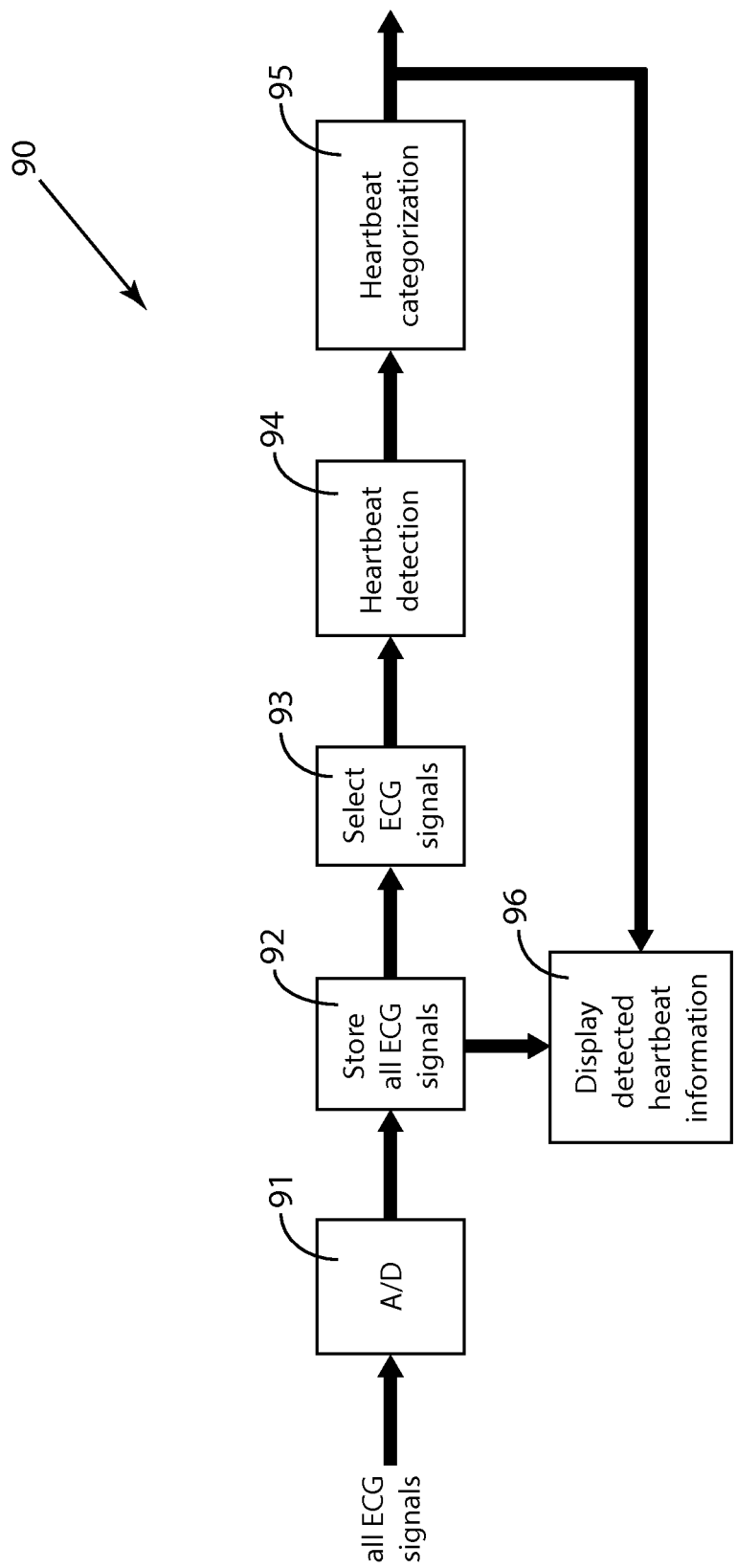
FIG. 14 is a high-level schematic block diagram of an embodiment of the inventive method in which all available ECG signals are digitized and stored and at least a portion of which are displayed.

FIG. 14 is a high-level schematic block diagram of an embodiment 90 of the inventive method in which all available ECG signals are digitized and stored and at least a portion of which are displayed. (The lines between the flow chart elements of embodiment 70 are shown as heavy lines to indicate that such lines may represent more than one ECG signal.) The ECG signals are digitized in flow chart element 91, and the digitized ECG signals are stored in available memory as represented by flow chart element 92. Flow chart element 93 represents the process of selecting ECG signals from among all the ECG signals, and flow chart elements 94 and 95 depict the steps of the inventive method to detect (94) and categorize (95) the heartbeats as described above in this application, such as by process portions 10A (and 10C) and 10B, respectively. Then flow chart element represent the step of displaying information descriptive of a detected heartbeat from the information stored in the step of flow chart element 92. For example, there may be a dozen or more ECG signals available, some of which may not be body surface signals, and many of these signals which are not among those selected and processed for detection and categorization may be displayed from storage to assist a user in the decision-making required during an interventional procedure.

Statistical studies on actual patient data from multiple patients have shown that comparison of the absolute velocity sum $G(t_i)$ against an adaptively-adjusted threshold T is a reliable detection method for heartbeats. Studies have also shown that the vector $F(t_D)$ is a reliable and robust measure by which to sort heartbeats into categories of heartbeats having similar morphology. The significance of this inventive method is that (1) heartbeats are detected early in the period of a heartbeat and (2) heartbeats are reliably categorized using measurements just at the instant ($t_D$) of detection rather than using a much larger amount of data related to the features of a heartbeat during its entire heartbeat period.

The value of $SC_L$, the limit value of $SCDA_q$, defines the region in N-space in which heartbeat vectors $F(t_D)$ must fall to be categorized as being similar to heartbeats in the category represented by template vector $F_q$. A larger value of $SC_L$ (smaller region subtended by the category) tends to increase the number of categories needed to categorize all of the heartbeats of a patient during a session of monitoring the patient's ECG.

Figure 15:
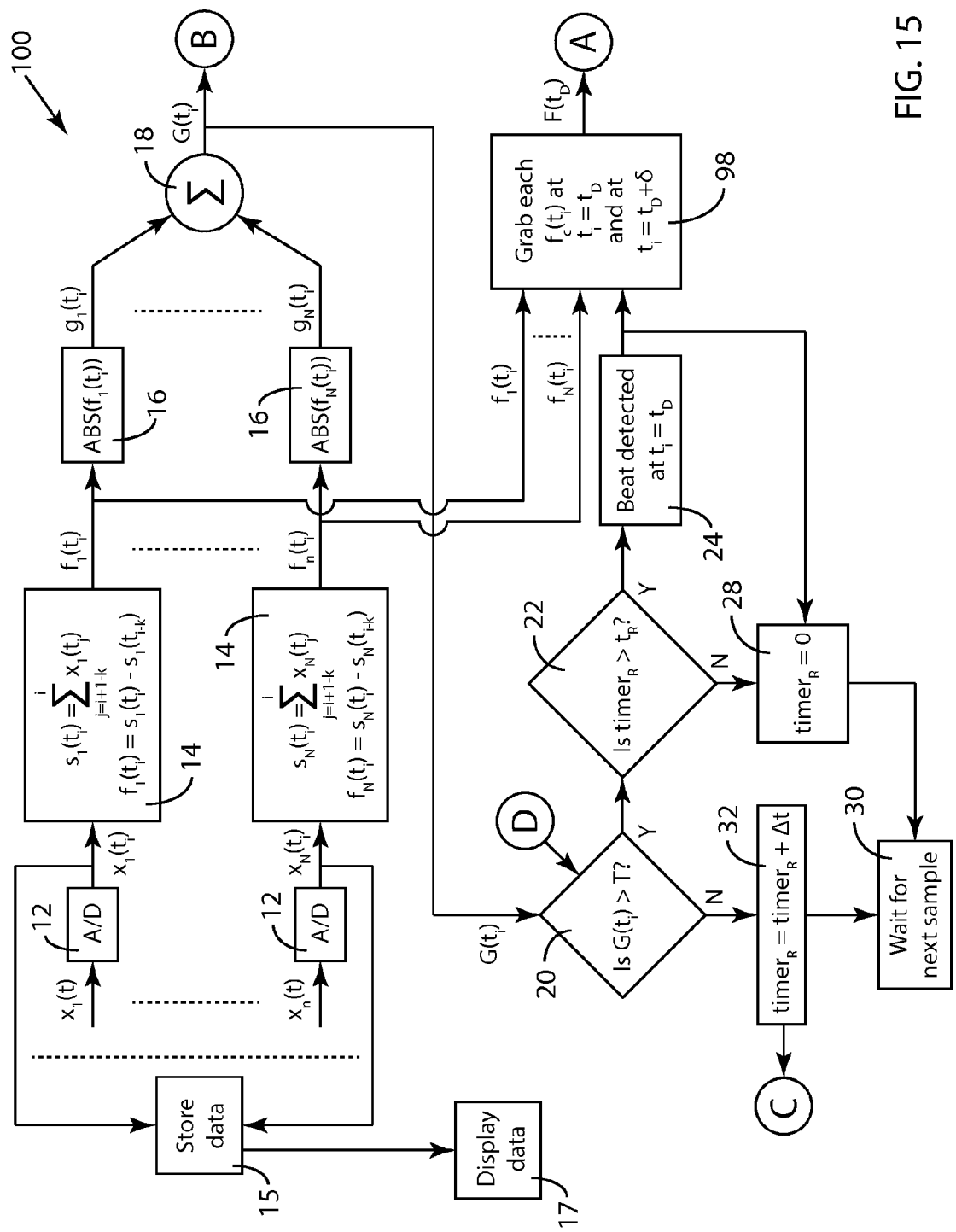
FIG. 15 is a schematic block diagram of an alternative embodiment of the heartbeat detection portion of the inventive method for heartbeat detection wherein after heartbeat detection, the vector representing a detected heartbeat is augmented with additional velocity components for categorization processing.

FIG. 15 is a schematic block diagram of an alternative embodiment 100 of the heartbeat detection portion of the inventive method for heartbeat detection wherein after heartbeat detection, vector $F(t_D)$ representing a detected heartbeat is augmented with additional velocity components for categorization processing. Embodiment 100 of FIG. 15 is identical to that of the embodiment of process portion 10A of FIG. 1 except that flow chart element 98 in FIG. 15 has replaced flow chart element 26 of FIG. 1.

In flow chart element 98, vector $F(t_D)$ is modified from that of flow chart element 26 in FIG. 1 such that vector f(tD) is now $$F(t_D) = \{f_1(t_D), \ldots, f_N(t_D), f_1(t_D+\delta), \ldots, f_N(t_D+\delta)\}$$

where $\delta$=a time period after heartbeat detection time $t_D$. In other words, vector $F(t_D)$ is now a vector associated with the heartbeat detected at time $t_D$ which has 2N components, the second set of which are the N velocities of the selected ECG signals at time $t_D+\delta$. In embodiment 100, vector $F(t_D)$ contains the N velocity components at detection time $t_D$ and N velocity components of the same ECG signals but measured at time $t_D+\delta$.

Figure 16A:
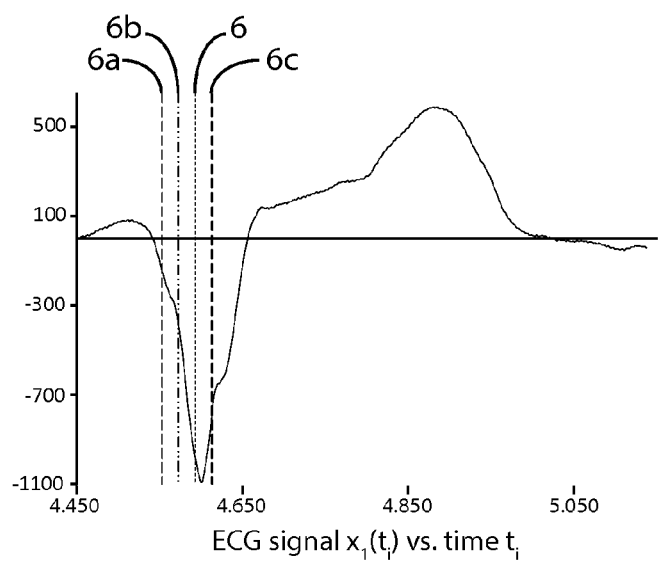
FIGS. 16A-16C are modified versions of FIGS. 11A-11C, showing a portion of the ECG signals of FIGS. 6A-6C which include a single detected heartbeat. The modifications in FIGS. 16A-16C for the example of FIGS. 6A-11D indicate the time at which additional velocity determinations are made, 20 milliseconds (msec) after a heartbeat is detected.
Figure 16B:
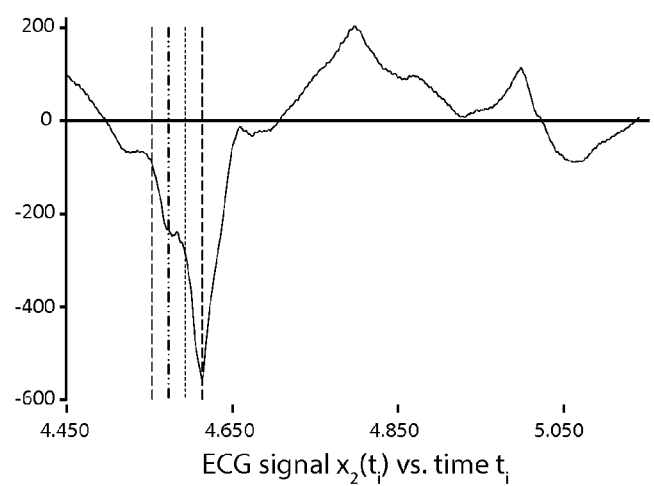
Figure 16C:
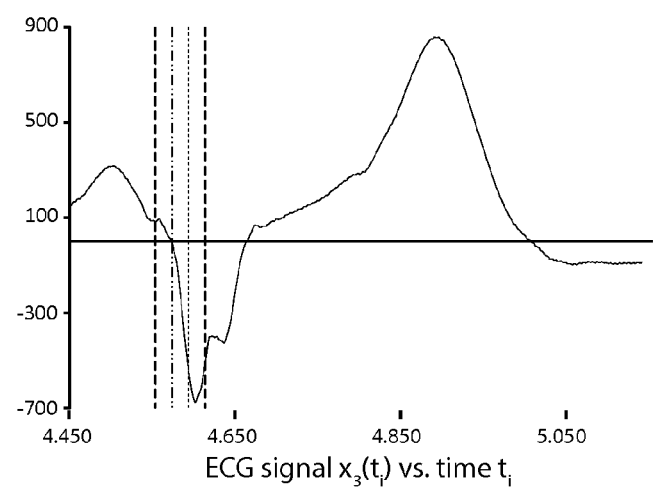

Adapting embodiment 100 to the example of FIGS. 6A-9D in which N=3, vector $F(t_D)$ now becomes $F(t_D)=\{f_1(t_D), f_2(t_D), f_3(t_D), f_1(t_{D+k}), f_2(t_{D+k}), f_N(t_{D+k})\}$ where k=20. Thus, the three additional velocity components of $F(t_D)$ are the velocities of the selected ECG signals measured one boxcar width k after detection time $t_D$. FIGS. 16A-16C are modified versions of FIGS. 11A-11C, showing a portion of the ECG signals of FIGS. 6A-6C which include a single detected heartbeat. The modifications in FIGS. 16A-16C for the example of FIGS. 6A-11D indicate the time at which additional velocity determinations are made, 20 msec after a heartbeat is detected. Vertical dotted line 6c is located at time 4.613 seconds, 20 msec after $t_D$=4.593 seconds for heartbeat #6.

As discussed above, in embodiment 100 for the example, vector $F(t_D)$ now has six velocity components instead of three. Categorization process 10B proceeds just as described above for the N=3 example. FIG. 17A is a table (similar to that of FIG. 10A) which shows detection times of the seven detected heartbeats during the time period of FIGS. 6A-6C and values of computed velocities and squared vector magnitudes of the velocity vector $F(t_D)=\{f_1(t_D), \ldots, f_n(t_D)\}$ generated in the alternative embodiment 100 of FIG. 15 (combined with FIGS. 2-4) for the selected ECG signals in FIGS. 6A-6C. FIG. 17A also includes four template vectors and their squared vector magnitudes as generated within this example. The heartbeat detection process of embodiment 100 is identical to that of process portion 10A, thus resulting in identical detected heartbeats #1-#7 as shown in FIG. 10A. FIG. 17A includes three additional columns which are the ECG signal velocities at $t_i=t_{D+k}$ (at $t_i=t_D+0.020$ seconds since k=20 samples and the sampling rate is 1,000 sps).

FIG. 17B is a table (similar to that of FIG. 10B) illustrating the computations made during the operation of this alternative embodiment during the time period shown in FIGS. 6A-6C. For this example, the value of preset threshold angle $\theta_L$ is 10°. The smaller value of preset threshold angle $\theta_L$ and the additional information provided by the second set of ECG signal velocities result in greater specificity of the categorization process.

In this brief (short time period of data) example, the alternative embodiment of the inventive method identified an additional heartbeat category characterized by heartbeat #5 (Template 6) while in the example summarized in FIG. 10B, heartbeat #5 was categorized as being similar to heartbeat #1 (characterized by Template 7).

Additional statistical studies on actual patient data have shown that the modified velocity vector $F(t_D)$ (having 2N components) improves the specificity of heartbeat categorization when compared with embodiment 10A of FIGS. 1-4. Such improvement in specificity is accomplished without applying smaller values for preset threshold angle $\theta_L$. In other words, adding a second velocity measurement into each velocity vector $F(t_D)$ yields similar improvements in categorization performance as tightening preset threshold angle $\theta_L$ for the single-velocity embodiment of the inventive method. In addition, the studies indicated that fewer but more precise templates were identified using embodiment 100 when compared with the embodiment 10A with a smaller preset threshold angle $\theta_L$.

While the principles of this invention have been described in connection with specific embodiments, it should be understood clearly that these descriptions are made only by way of example and are not intended to limit the scope of the invention.

The invention claimed is:

1. An automatic method for detecting heartbeats of a patient, the method comprising:
sensing two or more selected ECG signals; and
automatically processing the ECG signals with a programmable processor configured to:
determine a velocity for each of the selected signals;
sum together absolute values of each of the velocities;
compare the sum with a threshold T having a value about one-half of an expected maximum value of the sum; and
detect a heartbeat at a time $t_D$ of the velocity determinations when the sum is greater than the threshold T and when elapsed time since an immediately-previous heartbeat detection is greater than a preset refractory period $t_R$.

2. The automatic heartbeat detection method of claim 1 further including, when a heartbeat has been detected, the steps of:
forming a vector $F(t_D)$ the components of which are the velocities of each of the selected signals at the time $t_D$;
determining the angle between the vector $F(t_D)$ and a previously-stored template vector;
comparing the angle with a threshold angle; and
when the angle is less than the threshold angle, categorizing the heartbeat as similar to a heartbeat which corresponds to the template vector.

3. The automatic heartbeat detection method of claim 2 wherein the angle determination and comparison include the steps of:
computing a squared vector magnitude $SVM_D$ as the dot product $F(t_D) \cdot F(t_D)$;
computing the dot product $DP_q$ of $F(t_D)$ with a template vector $F_q$;
computing a squared vector magnitude $SVM_q$ as the dot product $F_q \cdot F_q$;
computing a signed squared cosine difference angle $SCDA_q$ as $SCDA_q = sgn(DP_q) * DP_q * DP_q / (SVM_D * SVM_q)$; and comparing $SCDA_q$ with a squared cosine threshold $SC_L$.

4. The automatic heartbeat detection method of claim 3 further including comparing the vector $F(t_D)$ with each of a plurality of template vectors to determine if the vector $F(t_D)$ is within the threshold angle of any of the plurality of template vectors.

5. The automatic heartbeat detection method of claim 4 wherein when the angle between the vector $F(t_D)$ and more than one of the plurality of template vectors is less than the threshold angle, categorizing the heartbeat as similar to a heartbeat which corresponds to the template vector having the smallest angle between itself and the vector $F(t_D)$.

6. The automatic heartbeat detection method of claim 5 wherein when the angle between the vector $F(t_D)$ and each of the plurality of template vectors is greater than or equal to the threshold angle, adding a template vector equal to the vector $F(t_D)$ to the plurality of template vectors.

7. The automatic heartbeat detection method of claim 5 wherein the patient is in a non-sedated state and further including the step of providing interventional treatment to the patient in a sedated state based on heartbeats categorized while the patient was in the non-sedated state.

8. The automatic heartbeat detection method of claim 2 further including comparing the vector $F(t_D)$ with each of a plurality of template vectors to determine if the vector $F(t_D)$ is within the threshold angle of any of the plurality of template vectors.

9. The automatic heartbeat detection method of claim 8 wherein when the angle between the vector $F(t_D)$ and more than one of the plurality of template vectors is less than the threshold angle, categorizing the heartbeat as similar to a heartbeat which corresponds to the template vector having the smallest angle between itself and the vector $F(t_D)$.

10. The automatic heartbeat detection method of claim 8 wherein when the angle between the vector $F(t_D)$ and each of the plurality of template vectors is greater than or equal to the threshold angle, adding a template vector equal to the vector $F(t_D)$ to the plurality of template vectors.

11. The automatic heartbeat detection method of claim 8 wherein the patient is in a non-sedated state and further including the step of providing interventional treatment to the patient in a sedated state based on heartbeats categorized while the patient was in the non-sedated state.

12. The automatic heartbeat detection method of claim 8 wherein each of the template vectors has a threshold angle associated therewith, not all of which have the same angle value.

13. The automatic heartbeat detection method of claim 8 wherein at least a portion of the plurality of template vectors are preset template vectors.

14. The automatic heartbeat detection method of claim 13 wherein each of the plurality of template vectors is a preset template vector.

15. The automatic heartbeat detection method of claim 2 further including a slot-plurality of template vector slots, the slot-plurality being greater than or equal to the plurality of template vectors and each template vector is in a corresponding template vector slot, wherein when the vector $F(t_D)$ is not within the threshold angle of any of the plurality of template vectors and an empty template vector slot is available, adding a template vector equal to the vector $F(t_D)$ to the plurality of template vectors.

16. The automatic heartbeat detection method of claim 15 wherein when no empty template vector slot is available, replacing one of the template vectors with a new template vector equal to the vector $F(t_D)$.

17. The automatic heartbeat detection method of claim 2 further including storing the categorized heartbeat.

18. The automatic heartbeat detection method of claim 17 further including displaying information descriptive of one or more stored heartbeats.

19. The automatic heartbeat detection method of claim 1 wherein determining the velocity of each of the selected signals includes:
digitizing each of the selected signals; and
filtering each of the digitized signals to generate the velocity for each selected signal.

20. The automatic heartbeat detection method of claim 19 wherein the filter is a first-difference filter.

21. The automatic heartbeat detection method of claim 20 wherein the first-difference filter is a boxcar filter.

22. The automatic heartbeat detection method of claim 1 further including adjusting the threshold T based on the maximum velocity sum during a preset time period $t_m$.

23. The automatic heartbeat detection method of claim 22 wherein when the preset time period $t_m$ has elapsed and when a preset detection failure time limit $t_L$ has not elapsed since previous heartbeats were detected, determining the threshold T by computing $T=T_p+(G_{max}/2-T_p)/4$ where $G_{max}$ is the maximum velocity sum during the elapsed preset time period $t_m$ and $T_p$ is the previous value of the threshold T.

24. The automatic heartbeat detection method of claim 23 wherein when preset time period $t_m$ has elapsed and when a preset detection failure time limit $t_L$ has elapsed since previous heartbeats were detected, setting the threshold T to $G_{max}/2$.

25. The automatic heartbeat detection method of claim 24 wherein $t_R$ is about 120 milliseconds, $t_m$ is about 2 seconds, and $t_L$ is about 5 seconds.

26. The automatic heartbeat detection method of claim 1 wherein three ECG signals are selected, and the signals form a quasi-orthogonal set.

27. The automatic heartbeat detection method of claim 1 wherein the ECG signals further include one or more ECG signals in addition to the selected ECG signals, and the method includes storing one or more of the additional ECG signals.

28. The automatic heartbeat method of claim 27 further including displaying information descriptive of a detected heartbeat.

29. The automatic heartbeat detection method of claim 1 further including, when a heartbeat has been detected, the steps of:
forming a vector $F(t_D)$ the components of which are the velocities of each of the selected signals at the time $t_D$ and the velocities of each of the selected signals at time $t_D+\delta$;
determining the angle between the vector $F(t_D)$ and a previously-stored template vector;
comparing the angle with a threshold angle; and
when the angle is less than the threshold angle, categorizing the heartbeat as similar to a heartbeat which corresponds to the template vector.

30. The automatic heartbeat detection method of claim 29 wherein the angle determination and comparison include the steps of:
computing a squared vector magnitude $SVM_D$ as the dot product $F(t_D) \cdot F(t_D)$;
computing the dot product $DP_q$ of $F(t_D)$ with a template vector $F_q$;
computing a squared vector magnitude $SVM_q$ as the dot product $F_q \cdot F_q$;
computing a signed squared cosine difference angle $SCDA_q$ as $SCDA_q = sgn(DP_q)*DP_q*DP_q/(SVM_D*SVM_q)$; and comparing $SCDA_q$ with a squared cosine threshold $SC_L$.

31. The automatic heartbeat detection method of claim 30 further including comparing the vector $F(t_D)$ with each of a plurality of template vectors to determine if the vector $F(t_D)$ is within the threshold angle of any of the plurality of template vectors.

32. The automatic heartbeat detection method of claim 31 wherein when the angle between the vector $F(t_D)$ and more than one of the plurality of template vectors is less than the threshold angle, categorizing the heartbeat as similar to a heartbeat which corresponds to the template vector having the smallest angle between itself and the vector $F(t_D)$.

33. The automatic heartbeat detection method of claim 32 wherein when the angle between the vector $F(t_D)$ and each of the plurality of template vectors is greater than or equal to the threshold angle, adding a template vector equal to the vector $F(t_D)$ to the plurality of template vectors.

34. The automatic heartbeat detection method of claim 32 wherein the patient is in a non-sedated state and further including the step of providing interventional treatment to the patient in a sedated state based on heartbeats categorized while the patient was in the non-sedated state.

35. The automatic heartbeat detection method of claim 29 further including comparing the vector $F(t_D)$ with each of a plurality of template vectors to determine if the vector $F(t_D)$ is within the threshold angle of any of the plurality of template vectors.

36. The automatic heartbeat detection method of claim 35 wherein when the angle between the vector $F(t_D)$ and more than one of the plurality of template vectors is less than the threshold angle, categorizing the heartbeat as similar to a heartbeat which corresponds to the template vector having the smallest angle between itself and the vector $F(t_D)$.

37. The automatic heartbeat detection method of claim 35 wherein when the angle between the vector $F(t_D)$ and each of the plurality of template vectors is greater than or equal to the threshold angle, adding a template vector equal to the vector $F(t_D)$ to the plurality of template vectors.

38. The automatic heartbeat detection method of claim 35 wherein the patient is in a non-sedated state and further including the step of providing interventional treatment to the patient in a sedated state based on heartbeats categorized while the patient was in the non-sedated state.

39. The automatic heartbeat detection method of claim 35 wherein each of the template vectors has a threshold angle associated therewith, not all of which have the same angle value.

40. The automatic heartbeat detection method of claim 35 wherein at least a portion of the plurality of template vectors are preset template vectors.

41. The automatic heartbeat detection method of claim 40 wherein each of the plurality of template vectors is a preset template vector.

42. The automatic heartbeat detection method of claim 29 further including a slot-plurality of template vector slots, the slot-plurality being greater than or equal to the plurality of template vectors and each template vector is in a corresponding template vector slot, wherein when the vector $F(t_D)$ is not within the threshold angle of any of the plurality of template vectors and an empty template vector slot is available, adding a template vector equal to the vector $F(t_D)$ to the plurality of template vectors.

43. The automatic heartbeat detection method of claim 42 wherein when no empty template vector slot is available, replacing one of the template vectors with a new template vector equal to the vector $F(t_D)$.

44. The automatic heartbeat detection method of claim 29 further including storing the categorized heartbeat.

45. The automatic heartbeat detection method of claim 44 further including displaying information descriptive of one or more stored heartbeats.

* * * * *

UNITED STATES PATENT AND TRADEMARK OFFICE
CERTIFICATE OF CORRECTION

| | |
|---|---|
| PATENT NO. | : 9,078,572 B2 |
| APPLICATION NO. | : 14/067561 |
| DATED | : July 14, 2015 |
| INVENTOR(S) | : Donald Brodnick |

Page 1 of 1

It is certified that error appears in the above-identified patent and that said Letters Patent is hereby corrected as shown below:

In the specification

Column 4 line 34, delete "6" and insert --δ--.

Column 7 line 21, between the words "set coefficients" insert --of--.

Column 7 line 26, delete "made" and insert --may--.

Column 7 line 30, after "50 Hz" delete the "," and insert a --.--.

Column 8 line 66, delete "|N|" and insert --|X|--.

Column 9 line 12, between the words "q checked" insert --is--.

Column 9 line 36, after "$\theta_q$" insert a --.-- and a space.

Column 9 line 57, delete ")$cos^2(25°$" and insert --$cos^2(25°)$--.

Column 9 line 57, delete "≅" and insert --≈--.

Column 10 line 9, delete "(angle $\theta_q$=) 180°." and insert --(angle $\theta_q$= 180°.)--.

Column 11 line 37, delete "begin" and insert --begins--.

Column 12 line 9, delete "to be" and insert --is--.

Column 12 line 36, delete "represent" and insert --represents--.

Column 13 line 2, delete "which".

Column 13 line 8, delete "region" and insert --regions--.

Column 14 line 24, delete ")$cos^2(25°$" and insert --$cos^2(25°)$--.

Column 14 line 29, delete "($\theta_g$113°)" and insert --($\theta_g$≈ 113°)--.

Column 14 line 39, delete "4.953" and insert --4.593--.

Column 15 line 14, delete "t=4.671" and insert --$t_i$=4.671--.

Column 16 line 8, delete "70" and insert --90--.

Column 16 line 19, delete "element represent" and insert --element 96 represents--.

Signed and Sealed this
Ninth Day of February, 2016

Michelle K. Lee
*Director of the United States Patent and Trademark Office*